United States Patent
Liao et al.

(10) Patent No.: US 10,385,013 B2
(45) Date of Patent: Aug. 20, 2019

(54) MICRO/NANO MATERIALS, PRODUCTS OBTAINED BY COVALENTLY MODIFYING SURFACE OF MICRO/NANO MATERIALS WITH HYDROPHILIC MATERIALS, AND METHOD FOR MAKING SAME

(71) Applicant: CHONGQING BOLANYING (BLY) BIOTECHNOLOGY CO., LTD., Chongqing (CN)

(72) Inventors: Fei Liao, Chongqing (CN); Gaobo Long, Chongqing (CN); Hai Yang, Chongqing (CN); Hu Feng, Chongqing (CN)

(73) Assignee: CHONGQING BOLANYING (BLY) BIOTECHNOLOGY CO., LTD., Chongqing (CN)

( * ) Notice: Subject to any disclaimer, the term of this patent is extended or adjusted under 35 U.S.C. 154(b) by 0 days.

(21) Appl. No.: 16/191,369

(22) Filed: Nov. 14, 2018

(65) Prior Publication Data
US 2019/0077746 A1    Mar. 14, 2019

Related U.S. Application Data

(63) Continuation of application No. PCT/CN2017/082374, filed on Apr. 28, 2017.

(30) Foreign Application Priority Data

Jun. 8, 2016 (CN) .......................... 2016 1 0405670
Oct. 28, 2016 (CN) .......................... 2016 1 0963764
Aug. 12, 2018 (CN) .......................... 2016 1 0662135

(51) Int. Cl.
| | | |
|---|---|---|
| C07C 269/04 | (2006.01) | |
| C07C 231/12 | (2006.01) | |
| C08G 81/02 | (2006.01) | |
| C08F 220/58 | (2006.01) | |
| C08F 222/38 | (2006.01) | |
| C08F 8/32 | (2006.01) | |
| C07C 227/12 | (2006.01) | |
| C07C 227/16 | (2006.01) | |
| C07C 269/06 | (2006.01) | |
| C07C 303/04 | (2006.01) | |
| C07C 303/32 | (2006.01) | |
| C07C 319/14 | (2006.01) | |
| C07C 231/08 | (2006.01) | |
| C07D 207/40 | (2006.01) | |
| C07C 67/08 | (2006.01) | |
| C08G 65/332 | (2006.01) | |

(Continued)

(52) U.S. Cl.
CPC ............ *C07C 269/04* (2013.01); *C07C 67/08* (2013.01); *C07C 227/12* (2013.01); *C07C 227/16* (2013.01); *C07C 231/08* (2013.01); *C07C 231/12* (2013.01); *C07C 269/06* (2013.01); *C07C 303/04* (2013.01); *C07C 303/32* (2013.01); *C07C 319/14* (2013.01); *C07D 207/40* (2013.01); *C08F 8/32* (2013.01); *C08F 220/58* (2013.01); *C08F 222/38* (2013.01); *C08G 65/332* (2013.01); *C08G 65/3348* (2013.01); *C08G 65/33306* (2013.01); *C08G 81/02* (2013.01)

(58) Field of Classification Search
CPC ... C07C 269/04; C07C 269/06; C07C 231/12; C07C 231/08; C07C 227/12; C07C 227/16; C07C 303/04; C07C 319/14; C07C 67/08; C08G 81/02; C08G 65/3348; C08G 65/33306; C08G 66/332; C08F 220/58; C08F 222/38; C08F 8/32; C07D 207/40
USPC .......................................................... 524/555
See application file for complete search history.

(56) References Cited

U.S. PATENT DOCUMENTS

2014/0024776 A1   1/2014   Charles et al.

FOREIGN PATENT DOCUMENTS

| CN | 102617810 A | * | 8/2012 |
|---|---|---|---|
| CN | 102617810 A | | 8/2012 |

(Continued)

OTHER PUBLICATIONS

Gaobo Long. Preparation and chracterization of hydrophilic magnetic submicron particles, Chongqing Medical University, Oct. 12, 2012, 16-17.

(Continued)

*Primary Examiner* — Michael Bernshteyn
(74) *Attorney, Agent, or Firm* — Wayne & Ken, LLC; Tony Hom

(57) ABSTRACT

Micro-nano materials, products obtained by covalently modifying the surfaces of micro/nano materials with hydrophilic materials, and methods for making the same. The micro/nano materials on the surfaces have carboxyl groups or/and pro-carboxyl groups which are converted into their active esters. The products are covalently modified by forming amide bonds between the active esters on the surfaces and the modification agents; where the modification agents are hydrophilic compounds and/or hydrophilic polymers bearing primary and/or secondary aliphatic amines. Monomers bearing carboxyl groups and/or pro-carboxyl groups are used to produce an adequate number of carboxyl groups and/or pro-carboxyl groups on the surface of a polymer material to be modified. The carboxyl groups and/or pro-carboxyl groups are converted into active esters. A reasonably-sized modification agent bearing primary and/or secondary amines, zwitterions and hydrophilic linear spacer arms is used to form amide bonds and obtain a covalently modified surface layer.

6 Claims, 8 Drawing Sheets

(51) Int. Cl.
     *C08G 65/333*     (2006.01)
     *C08G 65/334*     (2006.01)

(56) References Cited

FOREIGN PATENT DOCUMENTS

| CN | 106519147 A | * | 3/2017 |
| CN | 106519147 A | | 3/2017 |

OTHER PUBLICATIONS

Yunhui Zhai et al. Preparation of composite magnetic microspheres containing carboxyl and amine, New chemical materials, 2012, 40(10):29-31.

Gaobo Long et al. Facile one-step coating approach to magnetic submicron particles with poly(ethylene glycol) coats and abundant accessible carboxyl groups, International Journal of Nanomedicine, 2013, 8(default):791-807.

* cited by examiner

MICRO/NANO MATERIALS, PRODUCTS OBTAINED BY COVALENTLY MODIFYING SURFACE OF MICRO/NANO MATERIALS WITH HYDROPHILIC MATERIALS, AND METHOD FOR MAKING SAME

CROSS-REFERENCE TO RELATED APPLICATIONS

This application is a continuation of International Patent Application No. PCT/CN2017/082374, filed on Apr. 28, 2017, which claims the benefit of priorities from Chinese Application No. 201610405670.0, filed on Jun. 8, 2016, Chinese Application No. 201610662135.3, filed on Aug. 12, 2018 and Chinese Application No. 201610963764.X, filed on Oct. 28, 2016. The content of the aforementioned applications, including any intervening amendments thereto, are incorporated herein by reference.

TECHNOLOGICAL FIELD

The present disclosure is directed to biomedical micro/nano materials and surface modification, and particularly relates to micro/nano materials, products obtained by covalently modifying the surfaces of micro/nano materials with hydrophilic materials, and methods for making the same.

BACKGROUND

In the present disclosure, a substance having a molecular weight of less than 500 Daltons is denoted as a compound and a substance having a molecular weight of 500 Daltons or more is denoted as a polymer.

Covalent modification of the surfaces of the micro/nano materials with hydrophilic compounds/polymers, such as polyethylene glycol (PEG), compounds/polymers of zwitterion, or hydrophilic natural biopolymers (e.g., heparin and albumin, etc.) can reduce their non-specific adsorption to enhance their applications. Natural biopolymers are susceptible to non-specific adsorption of other biomolecules and still have strong non-specific adsorption of hydrophobic small molecules. For covalent modification of hydrophobic micro/nano materials, PEG and zwitterionic compounds are more attractive because their modification layers significantly reduce non-specific adsorption while possess stable and inert chemical structures. When the PEG chain is long enough, the modification effect is significant, otherwise a very high degree of modification is needed; the flexibility of the PEG chain itself limits the degree of modification; when the PEG density on the surface of the modified micro/nano materials is too large, the PEG chain still has non-specific adsorption of both proteins and hydrophobic small molecules. Therefore, the actual effect of modification with PEG alone is insufficient, making the covalent modification with zwitterions the sole promising way.

Zwitterions, also known as amphoteric ions, refer to functional groups/compounds with equal amounts of positive and negative charges. The zwitterions modification agent coated on the surface of the micro/nano material can significantly reduce non-specific adsorption. In addition, a mixture of a large number of intermolecular ion pairs also has a strong hydration ability and a weak non-specific adsorption. However, the accessible zwitterion modification agents have small sizes, leading to small modified areas and weak modification effects. Therefore, it is necessary to optimize the scheme of modification with zwitterions.

The design of the modification scheme firstly needs a selected covalent chemical reaction. Under mild conditions, a carboxyl group is easily activated into an active ester at a high yield, and then reacts with a primary or secondary aliphatic amine to form an amide bond at a high speed and high yield. The formation of amide bonds is thus a suitable covalent modification reaction, providing a high density of carboxyl groups on the surface of the micro/nano material for the conversion of such carboxyl into active esters which are reacted with a modification agent having the primary and/or secondary aliphatic amines.

The design of the modification scheme also needs the selection of the structure of the modification agent and the modification reaction conditions. A zwitterionic compound containing one or more primary and/or secondary aliphatic amines as a modification agent is usually insoluble in organic solvents but is easily soluble in an aqueous solution. This modification agent needs a modification reaction in an alkaline aqueous solution with an active ester on the surface of the micro/nano material. Otherwise, the amino reactivity is low and the degree of modification is insufficient, but the active ester is hydrolyzed in an alkaline aqueous solution so rapidly that the degree of modification still cannot be guaranteed. The active ester is stable under weakly acidic conditions, but the amine ion is ionized under such conditions and reacts slowly with the active ester, leading to uncertain degree of modification. The active ester reacts rapidly with the primary and secondary aliphatic amines in an inert organic solvent with high yields even at room temperature, but the zwitterionic compound is difficult to be dissolved in such an inert organic solvent. The solubility of nonionic compounds in inert organic solvents is generally high. A nonionic compound containing primary and/or secondary aliphatic amines and one or more functional groups which produce the amphoteric ion pairs by a simple reaction (i.e., pro-zwitterion groups), is designed as a modification agent. In an inert organic solvent, the modification agent forms amides with the active esters on the surface of the micro/nano material, and then the pro-zwitterion groups in situ are derived to produce zwitterions with high yields, giving a covalent modification layer of abundant zwitterions on the surface of the modified micro/nano material. This approach may be the sole strategy to generate a covalent modification layer of abundant zwitterions on the surface of the modified micro/nano material for negligible nonspecific adsorption of common substances.

1,3-propyl sultone can react with non-amide primary, secondary and tertiary aliphatic amines substituted by small alkyl groups to produce covalently bonded sulfonic acid. The number of sulfonic acid groups that are linked to a primary or secondary aliphatic amine is uncertain during covalent modification of a micro/nano material, yielding a charged surface that easily causes non-specific electrostatic adsorption of substances charged. Namely, the modification reaction with the micro/nano material is heterogeneous, and thus it is impossible to form a uniform zwitterion-modified neutral surface by controlling the amount of 1,3-propyl sultone. However, a tertiary amine bearing three small alkyl substituents can only be linked to one sulfonic acid and produce an amphoteric ion pair, thus being a suitable pro-zwitterion group. Therefore, a modification agent containing such tertiary amines is used to react with active esters on the surface of the micro/nano material in an inert organic solvent, and then 1,3-propyl sultone is used to convert such tertiary amines in situ to amphoteric ion pairs as completely as possible. This may be the only practical way to greatly reduce the non-specific adsorption by covalent modification of micro/nano materials with amphoteric ion pairs.

A hydrophilic modification agent bearing pro-zwitterion groups can significantly reduce the non-specific adsorption of the modified micro/nano materials only when the modification agent is coated on the surface of the micro/nano material at sufficient density, which requires a modification agent having a bulky size and a modification degree as high as possible. However, the steric hindrance of a bulky modification agent reduces both its reactivity with the active esters on the surface of the micro/nano material and the degree of modification. Inserting a linear linking arm between the modification agent and the active esters on the surface of the micro/nano material facilitates improving the coverage of the surface of the micro/nano material by the modification agent, while reducing the steric hindrance of the modification reaction. Covalent modification in an alternate mode with a small-sized modification agent bearing pro-zwitterion group(s) and then with a short PEG arm helps to enable the degree of modification in each step of the modification reactions. A multilayer covalent modification with a reasonably-sized modification agent bearing pro-zwitterion group(s) gradually increases the coverage of the surface of the micro/nano material by the modification agent, which is a necessary way to avoid the steric hindrance effect of the bulky modification agent itself and to enable the degree of modification. Inserting the linear linking arm directly or indirectly between the modification agent and the active esters on the micro/nano material surface facilitates improving both the coverage of the surface and the degree of modification. The modification reaction on the surface of the micro/nano material is heterogeneous with low repeatability, which requires a minimized number of modification reactions for a uniform product after modification. The use of a hydrophilic modification agent bearing pro-zwitterion group with a short linear hydrophilic linking arm to the primary and/or secondary amines (directly inserted), or the extension of the active esters on the surface obtained after each modification step to provide a linear linking arm indirectly, improves the coverage of the surface by the modification agent.

In order to guarantee the degrees of re-modification after each modification reaction for the formation of multiple modification layers, the pro-zwitterion modification agent used in each modification reaction must have sufficient numbers of carboxyl groups for conversion into active esters followed by covalent modification, but the potential electrostatic repulsions between these carboxyl groups may reduce both the reactivity of the modification agent itself with the active esters on the surface of the micro/nano material and the modification degree. The use of a neutral group which is a pro-carboxyl group, which can be converted into a carboxyl group through a simple reaction, can prevent the electrostatic repulsions between carboxyl groups from hindering the modification reaction, so as to guarantee the degree of modification. The use of monomers containing a large amount of neutral pro-carboxyl groups to prepare the micro/nano material by polymerization also facilitates deriving more active esters on the surface, which is an important strategy for making the micro/nano materials suitable for modification according to the present disclosure. Obviously, the use of a modification agent containing the pro-carboxyl group, the pro-zwitterion group, the primary/secondary aliphatic amine as the reactive functionality(ies) and the hydrophilic flexible linking arm(s) to such reactive functionality(ies), together with the use of monomer(s) containing neutral pro-carboxyl groups for polymerization to make a micro/nano material, is a necessary and comprehensively-optimized scheme for covalent modification.

In applications, it is desirable to retain the activity of the biomolecule immobilized on the surface of the micro/nano material through site-specific immobilization. In immunoassays, antibodies are often immobilized on the surface of micro/nano materials or form covalent adducts with micro/nano materials. Natural antibodies have several pairs of non-essential disulfide bonds away from the antigen binding site. The signal molecule/material having no sulfhydryl group and no disulfide bond on the surface can be conjugated to antibodies through selective covalent modification of the antibody disulfide bonds, which is advantageous for retaining the activities of both parts in the adducts and increasing the yields of the adducts. Hence, the present disclosure also utilizes a moiety free of sulfhydryl groups and disulfide bonds but selective for protein disulfide bonds, for the selective covalent labeling of an antibody by a protein having no sulfhydryl groups and no disulfide bonds on the surface, and the asymmetric cross-linking of a polymer free of sulfhydryl groups and disulfide bonds or such a small biochemical with the antibody, to give a higher activity in the resulting adduct.

Therefore, the core idea of the present disclosure is a systematically-optimized comprehensive solution for obtaining micro/nano materials bearing surface hydrophilicity and immobilized biomolecules with as high activities as possible, and the technical points thereof include: (1) optimization of the preparation of micro/nano materials to be modified: the micro/nano materials are prepared through the polymerization of special organic monomers where more aliphatic carboxyl or/and pro-carboxyl groups are formed on the surface of the resulting micro/nano material and converted into active esters at higher yields; (2) optimization of the modification agent structure: a hydrophilic modification agent of appropriate size having primary and/or secondary aliphatic amine, pro-zwitterion group(s) or/and carboxyl and/or pro-carboxyl groups(s), and a flexible/linear hydrophilic linking arm is employed as the modification agent; (3) optimization of the modification reaction: the optimized modification agent is used to form amide bonds in a high yield with the active esters on the surface of the micro/nano material in an inert organic solvent, thereby improving the degree of modification on the surface of the material; (4) optimization of the coverage of material surface with the modification agent: the coverage on the material surface with the modification agent is increased by multilayer covalent modifications obtained through repeated covalent modification to prevent the steric hindrance of a bulky hydrophilic modification agent from reducing the degree of modification and coverage; (5) the functional groups are provided with the flexible linking arm during the multilayer covalent modification process with the hydrophilic modification agent, and the specific functional groups on the surface of the covalently modified micro/nano material improves the retention of biological activity of immobilized macromolecules. The systematic optimization and integration of the various strategies effectively reduce the non-specific adsorption of common substances on the modified material and increase the activities of the immobilized macromolecules.

SUMMARY

The present disclosure is to provide a micro/nano material with surface bearing a functional group selected from one or more of a carboxyl group, a pro-carboxyl group, an active ester, a cation, an anion, a neutral hydrophilic group, a metal ion chelating group and a protein-disulfide-selective modification group, and a method for preparing the same. The present disclosure further provides a product obtained by covalently modifying the surface of the aforementioned micro/nano material with a hydrophilic material and a method for preparing the same. A special organic monomer containing the carboxyl group or/and the pro-carboxyl group is used in preparing the micro/nano materials to subsequently generate a sufficient number of carboxyl groups and then their active esters on the surface of the obtained micro/nano materials to be modified. An adequately-sized and hydrophilic modification agent bearing primary and/or secondary aliphatic amines, pro-zwitterion groups and a flexible linking arm is used to form an amide bond with the active esters on the surface of the micro/nano material to obtain a covalently modified layer, and a product bearing multilayer covalent modification is obtained by repeating covalent modification to improve the coverage on the surface of the micro/nano material by the modification agent, to reduce the non-specific adsorption of the product, and simultaneously to provide surface functional groups with a flexible linking arm.

The to-be-modified micro/nano material of the present disclosure contains the following type of functional groups on the surface: the carboxyl group, the pro-carboxyl group, the active ester, the cation, the anion, the neutral hydrophilic group, the metal ion chelating group or a protein-disulfide-selective modification group, or a mixture thereof. These functional groups on the surface of the micro/nano material to be modified are directly derived from the organic monomer used in the polymerization reaction to prepare the starting micro/nano material, or indirectly generated by performing derivation/conversion of the carboxyl group and/or the pro-carboxyl group originated from the organic monomers used in the polymerization reaction.

The present disclosure further discloses a method for preparing the micro/nano material to be modified. The micro/nano material to be modified is prepared by polymerization reaction of organic monomers. The organic monomers for the polymerization reaction directly provide the carboxyl group, the pro-carboxyl group, the active ester, the cation, the anion, the neutral hydrophilic group, the metal ion chelating group or the protein-disulfide-selective modification group, or a mixture thereof, on the surface of the micro/nano material; or the organic monomers used in the polymerization reaction directly provide a carboxyl group or a pro-carboxyl group on the surface which are then derived and chemically converted to provide indirectly the above-mentioned functional groups.

Further, the micro/nano materials to be modified include micro/nano material of organic polymers, composite micro/nano materials of organic polymers-inorganic micro/nano particles, and composite micro/nano materials of organic polymers-organic micro/nano particles. The micro/nano particles used for preparing the composite micro/nano materials include one of magnetic nanoparticles, quantum dots, up-conversion luminescent particles, organic polymer particles, and organic-inorganic composite particles, or a mixture thereof.

When preparing the micro/nano materials to be modified, the polymerization reaction uses specific organic monomers whose covalent structure contain both a functional group for polymerization and one type of the carboxyl group, the pro-carboxyl group, the active ester, the cation, the anion, the neutral hydrophilic group, the metal ion chelating group or the protein-disulfide-selective modification group, or a mixture thereof, and the ratio of the specific organic monomers to all of the monomers is at least 1%.

When preparing the micro/nano material particles to be modified, a water-in-oil or oil-in-water microemulsion system is used to disperse the monomers used in microemulsion systems for polymerization; as for bulky particles/membranes of the polymer materials, they are mechanically broken to obtain the required micro/nano material particles. When dispersed by the microemulsion system and then polymerized, the specific organic monomers are suitable for use alone or mixed in any ratio, as long as their solubility in the polymerization reaction phase meets the requirements.

The present disclosure also discloses products obtained by covalently modifying the surfaces of the micro/nano materials with hydrophilic modification agents, including products having the monolayer covalent modification and products possessing multilayer covalent modifications. The carboxyl groups and the pro-carboxyl groups on the surface of the micro/nano materials to be modified are converted into active esters to form amide bonds with a hydrophilic modification compound and/or a polymer as the modification agent containing a primary or/and a secondary aliphatic amine to achieve covalent modification and obtain a monolayer covalent modification. The active esters are regenerated repeatedly on the surface of the hydrophilic material covalently modified with the hydrophilic modification agent, and the hydrophilic compound and/or hydrophilic polymer containing the primary or/and secondary aliphatic amine is used to repeatedly form the amide bonds to perform covalent modification to obtain a product bearing multilayer covalent modification.

Further, one of the carboxyl group, the pro-carboxyl group, the cation, the anion, the neutral hydrophilic functional group, the active ester, the metal ion chelating group or the protein-disulfide-selective modification group, or a mixture thereof, is finally obtained on the surface of the covalently modified product.

The present disclosure also discloses a method for preparing the product by covalently modifying the surface of the micro/nano materials with a hydrophilic modification agent. The method includes the following steps:

a. when a micro/nanomaterial having a carboxyl group or/and a pro-carboxyl group on the surface as a micro/nanomaterial to be modified, forming an active ester of the carboxyl group or/and the pro-carboxyl group on the surface of the micro/nano material;

b. forming an amide bond by covalently modifying the micro/nano material on the surface having active ester obtained in step a with a hydrophilic compound and/or a hydrophilic polymer containing a primary aliphatic amine or/and a secondary aliphatic amine as a modification agent.

Further, the step b includes the following steps:

b1. forming an amide bond by covalently modifying the micro/nano material on the surface having active ester through step a with a hydrophilic compound and/or a hydrophilic polymer containing a primary aliphatic amine or/and a secondary aliphatic amine as a modification agent;

b2. converting a carboxyl group on the surface of micro/nano material obtained in step b1 into an active ester, or converting a pro-carboxyl group on the surface of micro/nano material into a carboxyl group and then into an active ester, or directly converting a pro-carboxyl group on the surface of micro/nano material into an active ester;

b3. repeating steps b1 and b2 according to the desired numbers of covalently modified layers.

Further, after the last covalent modification in step b, forming a functional group selected from one or more of a carboxyl group, a pro-carboxyl group, an active ester, a cation, an anion, a neutral hydrophilic group, a metal ion chelating group or a protein-disulfide-selective modification group, or a mixture thereof, on the surface of the micro/nano material.

Further, in step a, the active ester is derived from the carboxyl group or/and the pro-carboxyl group on the surface of the micro/nano material; such an active ester is produced by: directly converting the carboxyl group on the surface of the micro/nano material into the active ester, or converting the pro-carboxyl group on the surface of the micro/nano material into the carboxyl group which is then converted into the active ester, or converting the pro-carboxyl group on the surface of the micro/nano material into an aliphatic hydroxyl group and/or an aliphatic amine group which is then converted into the active ester using CDI or TPG, or directly converting the pro-carboxyl group on the surface of the micro/nano material into the active ester; reacting the active ester with a long linear amino acid to obtain a carboxyl group, reacting the active ester with a long linear amino acid to re-obtain a pro-carboxyl group or with cyclic acid anhydride to re-obtain a carboxyl group, so as to insert a linking arm between the carboxyl group or the pro-carboxyl group and the micro/nano material, and then converting a surface carboxyl group or a surface pro-carboxyl group obtained by derivation into the active ester.

In step b, the modification agent comprises an A type modification agent and a B type modification agent; the molecular weights of such an A type modification agent and a B type modification agent are 3000 Daltons or less.

The A type modification agent is a hydrophilic compound or a hydrophilic polymer containing a primary aliphatic amine or/and a secondary aliphatic amine; the hydrophilic compound or the hydrophilic polymer comprises one or more of N, N-dimethyl substituted aliphatic tertiary amine, N, N-diethyl substituted aliphatic tertiary amine and N, N-di-n-propyl substituted aliphatic tertiary amine; the A type modification agent is classified into an A1 subtype modification agent and an A2 subtype modification agent; the A1 subtype modification agent contains at least two primary and/or secondary aliphatic amines and at least one N,N-dialkyl substituted aliphatic tertiary amine group per molecule; and the A2 subtype modification agent contains only one primary or secondary aliphatic amine, but contains at least one N,N-dialkyl substituted aliphatic tertiary amine functional group.

in step b, the A1 subtype modification agent is used alone; or a mixture of the A1 subtype modification agent and the A2 subtype modification agent in any ratio is used; the sum of the molar amount of the primary and secondary aliphatic amines from the modification agent is in more than 10% excess to the molar amount of the active ester on the surface of the micro/nano material during modification; unless the last layer of covalent modification is to be completed, the A2 subtype modification agent is not used alone in step b.

The B type modification agent is a hydrophilic compound or polymer containing a primary aliphatic amine or/and a secondary aliphatic amine, without any one of N, N-dimethyl substituted aliphatic tertiary amine, N, N-diethyl substituted aliphatic tertiary amine and N, N-di-n-propyl substituted aliphatic tertiary amine, and is classified into a B1 subtype modification agent, a B2 subtype modification agent, a B3 subtype modification agent and a B4 subtype modification agent.

The B1 subtype modification agent has a linear structure, with a primary or secondary aliphatic amine at one end, and a carboxyl group or a pro-carboxyl group at the other end; the B2 subtype modification agent has a linear structure, with primary and/or secondary aliphatic amines at both ends; the B3 subtype modification agent has a linear structure, with a primary or secondary aliphatic amine at one end, and a methoxy or ethoxy group at the other end; the B4 subtype modification agent has a non-linear structure containing at least two primary aliphatic amines and/or secondary aliphatic amines.

The B1 subclass modification agent, the B2 subclass modification agent, the B3 subclass modification agent and the B4 subclass modification agent are used in the step b as follows. One of the B1 subtype modification agent, the B2 subtype modification agent and the B4 subtype modification agent, or a mixture thereof in any ratio, is used, and the sum of molar amount of the primary aliphatic amines and the secondary aliphatic amines from the modification agent is in more than 10% excess to the molar amount of the active esters on the surface of the micro/nano material; the B3 subtype modification agent regulates the ratio of the molar amount of the primary aliphatic amines and the secondary aliphatic amines from the B1 subtype modification agent, the B2 subtype modification agent or the B4 subtype modification agent; unless the last layer of covalent modification is to be completed, the B3 subtype modification agent is not used alone in step b.

The A type modification agent and the B type modification agent are mixed in any ratio; the sum of the molar amount of the primary aliphatic amine and the secondary aliphatic amine from the modification agents is in more than 10% excess to the molar amount of the active ester on the surface of the micro/nano material; unless the last layer of covalent modification is completed, a mixture consisting of only the A2 subtype modification agent and the B3 subtype modification agent in any ratio is not used in step b.

Further, the A type modification agent further comprises an A3 subtype modification agent, an A4 subtype modification agent, an A5 subtype modification agent and an A6 subtype modification agent.

The A3 subtype modification agent has a partial amphoteric ion pair and at least two primary aliphatic amines and/or secondary aliphatic amines which react with the active ester, or only one primary aliphatic amine or one secondary aliphatic amine which reacts with the active ester and at least one carboxyl group or one pro-carboxyl group.

The A4 subtype modification agent has a partial amphoteric ion pair and only one primary aliphatic amine or secondary aliphatic amine which reacts with the active ester, and does not contain the carboxyl group or the pro-carboxyl group suitable for subsequent modification to form the next layer; unless the last layer of covalent modification is to be completed, the A4 subtype modification agent is not used alone and is not mixed with the A2 subtype modification agent and the B3 subtype modification agent in any ratio in step b.

The A5 subtype modification agent is an anionic subtype modification agent, the A6 subtype modification agent is a cationic subtype modification agent; the A5 subtype modification agent comprises one or more sulfonic acid anions and/or phosphate anions; the A5 subtype modification agent containing one primary aliphatic amine or secondary aliphatic amine is classified into A5-1; the A5 subtype modification agent containing at least two primary aliphatic amines and/or secondary aliphatic amines is classified into A5-2; the A6 subtype modification agent contains one or more of quaternary cations or tertiary amine cations; the A6 subtype modification agent containing one primary aliphatic amine or secondary aliphatic amine is classified into A6-1;

and the A6 subtype modification agent containing at least two primary aliphatic amines and/or secondary aliphatic amines is classified into A6-2; the A5 subtype modification agent and the A6 subtype modification agent are combined for covalent modification of the micro/nano material with active ester on the surface to obtain an ion pair-modified layer.

In step b, the A3 subtype modification agent is used alone, or mixed with one or all of the A1 subtype modification agent, the A2 subtype modification agent, the A4 subtype modification agent, the B1 subtype modification agent, the B2 subtype modification agent and the B3 subtype modification agent in any ratio; unless the modification is to be completed, the ratio of the sum of the molar amount of the A1 subtype modification agent, the A3 subtype modification agent, the B1 subtype modification agent and the B2 subtype modification agent in a mixture modification agent is greater than 10%.

In step b, the A4 subtype modification agent is mixed with one or all of the A1 subtype modification agent, the A3 subtype modification agent, the B1 subtype modification agent, the B2 subtype modification agent and the B4 subtype modification agent in any ratio; unless the modification is to be completed, the ratio of the sum of the molar amount of the A1 subtype modification agent, the A3 subtype modification agent, the B1 subtype modification agent, the B2 subtype modification agent and the B4 subtype modification agent in the mixture modification agent is greater than 10%.

In step b, the A5 subtype modification agent and the A6 subtype modification agent are used in combination, and in the mixture, sulfonic acid anions or/and phosphate anions from the A5 subtype modification agent and quaternary cations and tertiary amine cations from the A6 subtype modification agent are equivalent in molar amount.

In step b1, when any of the modification agents, and mixtures thereof in any ratio, are used, the active ester on the surface micro/nano material is from CDI or TPG derivatives, and is suspended for reaction in an inert organic solvent or a neutral aqueous solution or in a mixed solvent thereof for modification for 10 minutes or more; or is suspended for reaction in an inert organic solvent for modification for 10 minutes or more.

In step b1, unless the A2 subtype modification agent or the B3 subtype modification agent is used alone, or a mixture thereof in any ratio are used, in an inert organic solvent, one of the active esters of haloacetic acid, N-bromoacetyl-6-aminocaproate, O-Ts glycolic acid, glycidyl-succinic acid monoester, N-trifluoroacetylglycine, 4-butyraldehyde acid and S-acetyl thioglycolatethe, or a mixture thereof in any ratio, is used to react with the primary aliphatic amine and the secondary aliphatic amine on the surface of a modified material to block any amine groups on the surface thereof and synchronously obtain the pro-carboxyl group; the molar amount of the active esters are in more than 10% excess to reactive aliphatic amine group on the surface of the micro/nano material; halogenated hydrocarbons, Ts esters, epoxy groups, trifluoroacetamide groups, aldehyde groups and acetyl protected sulfhydryl groups generated on the surface, as yielded, are pro-carboxyl groups.

In step b2, when the A1 subtype modification agent or/and the A2 subtype modification agent are used in the covalent modification process in the previous step, one of the active esters of haloacetic acid, N-bromoacetyl-6-aminocaproate, O-Ts glycolic acid, glycidyl-succinic acid monoester, N-trifluoroacetylglycine, 4-butyraldehyde acid and S-acetyl thioglycolate, or a mixture thereof in any ratio, is used to block the primary aliphatic amine and the secondary aliphatic amine remaining on the surface of the material, and 1,3-propyl sulfonyl ester which is in more than 10% excess to the molar amount of the dialkyl-substituted tertiary amine on the surface of the modified material is used in an inert organic solvent to convert an alkyl tertiary amine from the A1 subtype modification agent or the A2 subtype modification agent into a zwitterion with the quaternary ammonium adjacent to the sulfonic acid; and then the carboxyl group and the pro-carboxyl group on the surface of the covalently modified product are converted into the active esters.

In step b2, when the A1 subtype modification agent or the A2 subtype modification agent is not used in the covalent modification process in the previous step, one of active esters of haloacetic acid, N-bromoacetyl-6-aminocaproic acid, O-Ts hydroxyacetic acid, glycidyl-succinic acid monoester, S-acetylmercaptoacetic acid, N-trifluoroacetylglycine and 4-butyraldehyde, or a mixture thereof in any ratio, is used to block the primary aliphatic amine and the secondary aliphatic amine remaining on the surface of the modified product to obtain a pro-carboxyl group; and the carboxyl group and the pro-carboxyl group on the surface of the covalently modified product are converted into active esters.

In step b2, the active ester on the surface of the covalently modified product reacts with a long linear amino acid to obtain a carboxyl group, or reacts with a linear polyamine containing multiple primary aliphatic amines to obtain an aliphatic amine group for reacting with a material containing a pro-carboxyl group and an active ester to regain pro-carboxyl groups or for reacting with a cyclic anhydride to regain carboxyl groups, a linking arm is inserted between the surface carboxyl groups or pro-carboxyl group and the covalently modified product, and then the carboxyl group or pro-carboxyl group derived and converted on the surface of the covalently modified product are further converted to active esters.

In step c, in the previous covalent modification process, the B1 subtype modification agent having the aliphatic amine group on one end and the carboxyl group on the other end is used alone to directly obtain a surface layer carboxyl group; when one of the B2 subtype modification agent and the B4 subtype modification agent, or a mixture thereof in any ratio, is used alone, in an inert organic solvent, one of active esters of haloacetic acid ester, N-bromoacetyl-6-aminocaproic acid ester, O-Ts hydroxyacetic acid ester, glycidyl-succinic acid ester, N-trifluoroacetylglycine ester, 4-butyraldehyde acid ester, S-acetylmercaptoacetic acid ester and disulfide-selective modification group corresponding material, or a mixture thereof in any ratio, is used to react with the primary aliphatic amine and the secondary aliphatic amine on the surface of the modified material; and the molar amount of the active esters is in more than 10% excess to the molar amount of the reactive amine groups on the surface of the micro/nanomaterial, and one of the corresponding hydrocarbon, O-Ts ester, epoxy, trifluoroacetamide, aldehyde, protecting thiol, disulfide-selective modification group, or a mixture of the above surface functional groups, is generated on the surface.

In step c, in the previous covalent modification process, the A2 subtype modification agent is used alone to obtain the cationic surface functional group of the alkyl-substituted tertiary amine, for example, an excess of 1,3-propyl sultone is used to convert the alkyl tertiary amine on the surface of the A2 subtype modification agent into amphoteric ions with the quaternary ammonium adjacent to the sulfonic acid to obtain a zwitterionic surface; the B3 subtype modification agent is used alone to obtain a neutral and inert hydrophilic surface functional group.

In step c, the carboxyl group or the pro-carboxyl group on the surface of the covalently modified product is converted into an active ester, to react with a long linear amino acid to re-obtain a carboxyl group, or to react with a linear polyamine containing multiple primary aliphatic amines to obtain an aliphatic amine group, for reacting with a material containing a pro-carboxyl group and an active ester to regain a pro-carboxyl group or reacting with a cyclic acid anhydride to regain a carboxyl group or reacting with an active ester containing other functional groups to obtain other forms of surface functional groups, thereby inserting a linking arm between the resulting surface functional groups and the modified product.

Further, the protein-disulfide-selective modification group comprises two active functional groups enabling Michael addition and/or nucleophilic substitution reaction with a sulfhydryl group, with no more than 10 covalent bonds located between the two reactive functional groups; and a carboxyl group for conjugation via forming an amide bond with other components.

The reactive group undergoing Michael addition reaction with sulfhydryl group is an acryloyl group, or a vinyl sulfone group, and when functioning alone, acts as a pro-carboxyl group; its reaction centre is β position of carbonyl in acroleyl group and β olefin carbon atom of sulfonyl group.

The reactive group undergoing nucleophilic substitution reaction with a sulfhydryl group is an alkyl containing one or more of chlorine, bromine, iodine, trifluoroacetate, p-toluenesulfonate at α-saturated carbon atom of a carbonyl group, a sulfone group, an olefin, and an aromatic ring, and a group from which the alkyl is derived after the Michael-addition of the protein sulfhydryl group, and such a reactive group acting alone is a pro-carboxyl group; chlorine, bromine, iodine, trifluoroacetate, and p-toluenesulfonate are the leaving group X of the nucleophilic substitution reaction, and the reaction center of the nucleophilic substitution is an α-saturated carbon atom corresponding to the carbonyl group, the sulfone group, the olefin and the aromatic ring.

In the protein-disulfide-selective modification group, the fragment linking two reaction centers of sulfhydryl groups does not contain a ring or a trialkyl substituent, and a five- or six-membered ring as covalently linked fragment attach to two active groups reactive with the protein sulfhydryl groups to the ring simultaneously. The carboxyl group contained in the protein disulfide selective modification functional group for covalently linking with the micro/nano material, is converted into an active ester, an acid anhydride or an acid chloride to react with the primary and secondary amine on the surface of the micro/nano material, so as to obtain the protein-disulfide-selective modification group on the surface of the modified micro/nano material. When the protein-disulfide-selective modification group is used, the disulfide bond on the surface of the target protein is first reduced to two spatially adjacent free sulfhydryl groups by trialkylphosphine, and then such two spatially adjacent protein sulfhydryl groups simultaneously react with the two reaction centers in the protein-disulfide-selective modification group on the surface of the micro/nano material, thereby achieving site-selective covalent attachment/immobilization of the protein.

The application of the protein-disulfide-selective modification group has the following characteristics: the carboxyl group contained in the protein-disulfide-selective modification group is covalently linked to the polymer/small molecule amine group having no sulfhydryl groups and disulfide bonds on the surface, to obtain the protein-disulfide-selective modification group and thus a selective modification or labeling agent for disulfide bonds on protein surface; trialkylphosphine is used to reduce the surface disulfide bond of the protein to two adjacent free sulfhydryl groups, to simultaneously react with the two reactive groups in the protein-disulfide-selective modification group in the selective modification/labeling agent described above, thereby achieving the site-specific covalent attachment or labeling.

Advantageous effects of the present disclosure are as follows: the present disclosure uses the special organic monomers containing the carboxyl groups or/and the pro-carboxyl groups in the preparation of the micro/nano material in order to finally generate enough active esters on the surface of the micro/nano material to be modified; uses an adequately-sized modification agent bearing the primary and/or the secondary aliphatic amine(s), the pro-zwitterion groups and a flexible hydrophilic linking arm to reduce the steric hindrance in the modification reaction; the modification agent forms an amide bond with the active ester on the surface of the micro/nano material to be modified in an inert organic solvent to obtain a high-density covalently modified layer, in order to guarantee the modification degree; the covalent modification is repeated to produce multilayer covalent modification for improving the coverage on the surface of the material by the modification agent and reducing the non-specific adsorption of the product, thereby avoiding the steric hindrance of the desired modification when directly using a bulky modification agent; a linking arm for each layer of modification and surface functional groups are provided during the multilayer covalent modifications to increase the activity of the immobilized biomolecules. The accumulation of the above beneficial effects finally enables the product prepared by covalently modifying the surface of the micro/nano material with the hydrophilic material to be highly hydrophilic, bear negligible non-specific adsorption of proteins, nucleic acids and hydrophobic small molecules, and become suitable for retaining the activity of the immobilized biomolecules.

BRIEF DESCRIPTION OF THE DRAWINGS

The present disclosure is described below in conjunction with the drawings and embodiments.

DETAILED DESCRIPTION OF EMBODIMENTS

Figure 1:
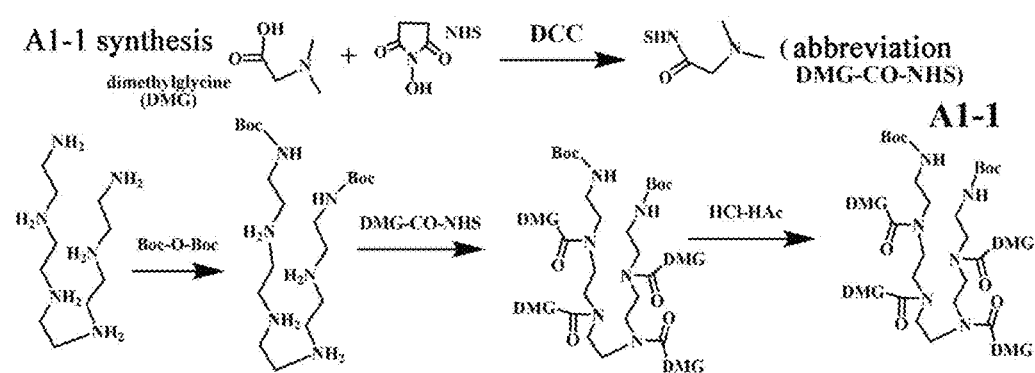
FIG. 1 shows the production of A1-1 type modification agent.

Suitable materials and their properties are as follows.

1. Cyclic anhydride includes cyclosuccinic anhydride, cycloglutaric anhydride and polymaleic anhydride. Halogenated hydrocarbon refers to the hydrocarbon with substituted chlorine, bromine or iodine at the primary carbon atom of saturated aliphatic hydrocarbon, α-position of the carbonyl group. Ts represents p-toluenesulfonyl, and Ts ester is an ester formed by Ts and a primary or secondary alcohol. Boc is a tert-butoxycarbonyl group.

2. Dicyclohexylcarbodiimide (DCC), N-hydroxysuccinimide (NHS), sodium salt of N-hydroxysuccinimide sulfonate (SNHS); 1-(3-dimethylaminopropyl)-3-Ethylcarbodiimide hydrochloride (EDC); N,N'-carbonyldiimidazole (CDI), triphosine (TPG); an ester of carboxyl group to p-nitrophenol, NHS or SNHS, carbonyl imidazole formed by hydroxyl and amino groups with the excess of CDI, carbonate ester formed by a hydroxyl group and an amino group with the excess of TPG, and a mixed anhydride formed by carboxylic acid with CDI or TPG, are the activated forms of carboxyl in the present disclosure and are collectively referred to as active esters.

3. An organic solvent which does not react with active esters of carboxyl group, cyclic anhydride, an epoxy group, Ts ester, halogenated hydrocarbon, aldehyde group or thioester is called as an inert organic solvent, and is represented by tetrahydrofuran (THF), 1,4-dioxane, dimethylforamide and dimethyl sulfoxide.

4. Linear polyamine refers to the current polyamines linked by ethyl or n-propyl, including diethylenetriamine, triethylenetetramine, tetraethylenepentamine, pentaethylenehexamine, di-n-propylene triamine, tri-n-propylene Tetraamine, tetra-n-propylene pentamine, penta-n-propylene hexamine.

5. Polyethyleneimine (PEI), with the following figures indicating the average molecular weight; ethylenediamine-terminated PEI is represented by $NH_2$-PEI; dendrimer whose terminal group is amino group is represented by Dendrimer-$NH_2$.

6. Polyethylene glycol (PEG), with number followed indicating the average molecular weight, is a linear chain and has hydroxyl groups at two ends. PEG with the amino group on one end and the hydroxyl group on the other end is represented by PEG-$NH_2$; the PEG with the amino group on one end and the carboxyl group on the other end is represented by $NH_2$-PEG-COOH. The polyethylene glycol having the carboxyl group at both ends is represented by COOH-PEG-COOH.

7. Branched PEG is a structure having multiple linearly stretched PEG chains (n-PEG), which is formed by linking a linear polyamine, a polyhydroxy compound, Dendrimer-$NH_2$, an amino acid having multiple amino groups, a polyhydroxy acid having multiple hydroxyl groups, or a compound having multiple free sulfhydryl groups through an amide or a carboxylate ester bond or thioether bond.

Chemical nature of the pro-carboxyl group is as follows.

A pro-carboxyl group refers to a group capable of forming the carboxyl group or the active ester of carboxyl through a reaction within three steps under mild conditions (70° C. or less). The pro-carboxyl group includes primary or secondary aliphatic alcohol, primary or secondary aliphatic amine, and primary/secondary aliphatic alcohol and primary/secondary aliphatic amine protected with trifluoroacetyl, tert-butoxycarbonyl or phthalic anhydride; halogenated hydrocarbon with substituted chlorine, bromine or iodine at α-position carbon atom of the carbonyl group; O-Ts hydroxyacetamide or glycolic acid ester and p-toluenesulfonate; epoxy group such as glycidol derivatives; aldehyde group, sulfo protected sulfhydryl group, and acetyl protecting sulfhydryl group. In addition, the active ester itself is a pro-carboxyl group which can form a carboxyl group through a reaction with amino acid or through hydroxide hydrolysis. Each sulfhydryl reactive group in the protein disulfide selective modification functional group is a pro-carboxyl group when functioning alone, and is converted into the carboxyl group after reaction with thioglycolic acid. The method for converting the pro-carboxyl group into aliphatic carboxyl group or directly converting the same to active ester is described below.

1) The primary or secondary aliphatic amine or primary or secondary aliphatic alcohol as the pro-carboxyl group reacts with cyclic anhydride in an inert organic solvent at 70° C. for 0.5 hour or longer to produce the carboxyl group. Then, the carboxyl group reacts with excessive CDI or TPG at 70° C. for 30 minutes or longer to form the active ester.

2) Halogenated hydrocarbon, Ts ester or epoxy group as pro-carboxyl group reacts with a linear amino acid (e.g., glycine, 3-alanine and 6-aminocaproic acid) having an amino group at one end and a carboxyl group at the other end, or a linear mercapto-carboxylic acid (e.g., thioglycolic acid and 3-mercaptopropionic acid) having a sulfhydryl group at one end and a carboxyl group at the other end, at 70° C. for 30 minutes or longer to give the aliphatic carboxyl groups.

3) The primary or secondary aliphatic amine or primary or secondary aliphatic alcohol protected by trifluoroacetyl, as pro-carboxyl group, are hydrolyzed in a mixed solvent of an inert organic solvent and water using 0.1 M or more of sodium/potassium hydroxide at 70° C. for 30 minutes or more to expose hydroxyl or amino groups. The hydroxyl or amino groups are then converted into aliphatic carboxyl groups or active esters thereof according to the conversion methods of the hydroxyl or amino groups.

4) Boc-protected primary or secondary aliphatic amine or primary or secondary aliphatic alcohol as pro-carboxyl group is treated using one of acetic acid, trifluoroacetic acid and hydrochloric acid, or a mixture thereof, to remove Boc and to expose hydroxyl or amino groups. The hydroxyl groups or amino groups are converted into aliphatic carboxyl groups or active esters thereof according to the conversion methods of the hydroxyl or amino groups.

5) Phthalic anhydride-protected primary aliphatic amine as pro-carboxyl group is hydrolyzed in a mixed solvent of an inert organic solvent and water using hydrazine to expose amino group. The amino group is then converted into an aliphatic carboxyl group or active ester thereof according to the conversion method of amino groups.

6) The aldehyde group as pro-carboxyl group reacts with glycine or 6-aminocaproic acid and then is reduced to a carboxyl group with $NaBH_4$, or reduced by $NaBH_4$ to obtain a hydroxyl group which is converted into an aliphatic carboxyl group according to the conversion method of hydroxyl groups or directly converted into an active ester thereof; or reacts with thioglycolic acid and then is reduced to obtain a thioether-linked aliphatic carboxyl group.

7) Sulfonic acid-protected sulfhydryl groups and S-acetyl-protected sulfhydryl groups as pro-carboxyl groups is reduced with NaBH4 to obtain a sulfhydryl group, followed by reaction with haloacetic acid, O-Ts acetic acid or the monoester of glycidol and succinic anhydride to obtain a carboxyl group. The carboxylation method of the S-acetyl-protected thiol group is to release the acetyl group with hydroxylamine to obtain a free sulfhydryl group, and then convert the thiol group into an aliphatic carboxy group.

8) In the method for production of multilayer covalent modification on the surface of the micro/nano material with a hydrophilic material, the method for converting a pro-carboxyl group to a carboxyl group is required to be compatible with the micro/nano material to be modified, that is, after a pro-carboxyl group on the surface of the micro/nano material is converted to a carboxyl group or directly converted to its active ester, the basic physicochemical properties of the micro/nano material remain, that is, the pro-carboxyl group can only be converted to a carboxyl group or an active ester thereof under mild conditions.

The present disclosure discloses a micro/nano material with a surface containing a functional group selected from one or more of a carboxyl group, a pro-carboxyl group, active ester, a cation, an anion, a neutral hydrophilic group, a metal ion chelating group or a protein-disulfide-selective modification group. These functional groups are directly derived from special organic monomers used in the polymerization reaction system for preparing the micro/nano material, or are produced through derivatization of carboxyl groups and/or pro-carboxyl groups carried on the special organic monomers. These special organic monomers include organic monomers containing both a functional group for polymerization and a functional group selected from one or more of the carboxyl group, the pro-carboxyl group, the active ester, the cation, the anion, the neutral hydrophilic group, the metal ion chelating group or the protein-disulfide-selective modification group. The micro/nano material is prepared using a special organic monomer containing a carboxyl group or/and a pro-carboxyl group to directly obtain a carboxyl group or/and a pro-carboxyl group, and then to derive into other functional groups by: converting the carboxyl group and/or pro-carboxyl group into an active ester; reacting the active ester with Nα, Nα-dicarboxymethyl lysine to obtain a metal ion chelating functional group, or reacting the active ester with N,N-dimethylethylenediamine to obtain an organic cationic functional group, or reacting the active ester with taurine to obtain an anionic functional group, or reacting the active ester with ethanolamine to obtain a hydroxyl group followed by a reaction with p-toluenesulfonyl chloride to obtain a Ts ester; reacting the active ester with a linear polyamine to obtain an aliphatic amine group followed by a reaction with an active ester of a protein disulfide selective modification functional group to obtain a protein disulfide-selective modification group, or a reaction with an active ester corresponding to glycidyl-succinic acid monoester, 4-butyraldehyde acid or S-acetyl thioglycolate to obtain a corresponding functional group; reacting the active ester with a long linear amino acid to obtain a carboxyl group, whose derivatization mode is actually to insert a flexible linking arm between the surface functional groups and the modified materials.

The present disclosure further discloses a method for preparing the micro/nano material to be modified. The micro/nano material is prepared by polymerization reaction of organic monomers, and the resulting surface contains a functional group selected from one or more of the carboxyl group, the pro-carboxyl group, the active ester, the cation, the anion, the neutral hydrophilic group, the metal ion chelating group and the protein-disulfide-selective modification group. These functional groups are directly or indirectly derived from the organic monomer for polymerization. Of course, the method includes performing a conversion of a carboxyl group or/and a pro-carboxyl group on the surface of the micro/nano material to indirectly produce other forms of functional groups, which belongs to a structure that can be deduced from the technical solution of the present disclosure, and fall within an equivalent of the technical solution of the present disclosure.

In this embodiment, the micro/nano material includes organic polymers, organic polymer-inorganic micro/nano-particle composites or organic polymer-organic micro/nano-particle composites. The micro/nanoparticles used in the process for making the composite micro/nano materials include one of magnetic nanoparticles, quantum dots, up-conversion luminescent particles, organic polymer micro/nanoparticles, organic-inorganic composite micro/nanoparticles or a mixture thereof in any ratio.

When preparing the micro/nano materials, the polymerization reaction system uses special organic monomers. A product is obtained by reacting a material containing a functional group selected from one or more of a carboxyl group, a pro-carboxyl group, a cation, an anion, a neutral hydrophilic functional group, a metal ion chelating functional group or a protein disulfide selective modification functional group with a symmetric acid anhydride and/or an active ester containing a functional group for polymerization. A product is obtained by reacting a material containing a primary and/or secondary aliphatic amine but without a carboxyl group or a pro-carboxyl group with cyclic anhydride containing a functional group for polymerization and/or with the active ester containing both the functional group for polymerization and the pro-carboxyl group. Both of the above products are candidates of special organic monomers. In the polymerization reaction system, the summed molar amount of each of the special organic monomer is not less than 1% of the total molar amount of all monomers. An amide linkage product, obtained by reacting A type modification agent and B type modification agent containing aliphatic carboxyl group and/or pro-carboxyl group with the symmetric anhydride, active ester or acid chloride having the functional group for the polymerization reaction, is one of the representatives of the special organic monomers of the present disclosure. Also, an amide linkage product obtained by reacting A type modification agent or B type modification agent without aliphatic carboxyl groups and pro-carboxyl groups with a cyclic anhydride having a functional group for polymerization is one of the representatives of the special organic monomers of the present disclosure.

When preparing the micro/nano materials to be modified, the water-in-oil or oil-in-water microemulsion system is used to disperse monomers into the microemulsion system followed by polymerization, or bulky particles/films of the polymers are broken mechanically to obtain desired micro/nano materials. When polymerized after being dispersed in the microemulsion system, the special organic monomers used herein are suitable for use alone or mixing in any ratio, and this requires that the total concentration of polymerization functional groups derived from such special organic monomers and cross-linking agents for polymerization is greater than 0.10 mol/L in the dispersed polymerization phase.

The present disclosure further discloses a product obtained by covalently modifying the surface of the micro/nano material with hydrophilic material, including the product obtained through a monolayer or multilayer covalent modification(s). A micro/nano material with a surface having a carboxyl group or/and a pro-carboxyl group is used as the micro/nano material for modification, the carboxyl group and the pro-carboxyl group on the surface are converted into active esters, and then covalently modified with a hydrophilic compound and/or a polymer containing the primary or/and secondary aliphatic amine as the modification agent to form amide bonds and obtain a product bearing the monolayer covalent modification. The active ester is repeatedly regenerated on the surface of the modified hydrophilic material, to form amide bonds by using a hydrophilic compound and/or polymer containing the primary or/and secondary aliphatic amine as the modification agent to obtain a product bearing multilayer covalent modification. The purpose of this covalent modification process is to reduce the non-specific adsorption of the surface of the modified material, and simultaneously to provide a flexible arm required by the immobilized biomolecules through multiple layers of modification. The modification process is highly dynamic, and can determine, according to the needs, the required number of covalent modification layers and the modification agent used in the last step to directly obtain the desired surface functional groups.

In this embodiment, the functional group finally obtained on the surface of the covalently modified product is one or more of a carboxyl group, a pro-carboxyl group, an active ester, a cation, an anion, a neutral hydrophilic group, a metal ion chelating group, or protein-disulfide-selective modification group, or a mixture thereof. These functional groups are used for the covalently modified product to form a covalent adducts or reversible complexes with other materials.

The present disclosure further discloses a method for preparing a product by covalently modifying the surface of the micro/nano material with hydrophilic material, including the following steps:

a. forming active esters of the carboxyl groups on the surface of the micro/nano material; wherein a micro/nano material having a carboxyl group or/and a pro-carboxyl group on the surface is used as a micro/nano material to be modified, and the carboxyl groups or/and the pro-carboxyl groups on the surface are converted into active esters. The micro/nano material refers to an organic polymer having at least one dimension of no more than 100 μm, or a composite of such organic polymers and organic or inorganic micro/nano materials with two overall dimensions. In one aspect, the micro/nano material is a particle with a particle size of less than 100 μm, which may be spherical or approximately spherical. In another aspect, the micro/nano material is a film having a thickness of less than 100 μm, the area of which is not limited, including a free film or a film attached to the surface of various shapes of solids.

b. The micro/nano material bearing active esters on surface forms amide bonds with a hydrophilic compound or a hydrophilic polymer as a modification agent containing the primary or/and secondary aliphatic amine to achieve covalent modification.

In the modification process, the pro-carboxyl groups on the surface of the starting micro/nano material is generally converted into an aliphatic carboxyl group, which after being dried reacts with DCC and NHS in an inert organic solvent to form an active ester, or reacts with CDI or TPG to directly converted into an active ester, or reacts with EDC and NHS or SNHS in an inorganic buffer of pH 5.0-8.0 or an organic buffer free of primary and secondary aliphatic amines to form an active ester. The amino or pro-carboxyl groups on the surface of the starting micro/nano material, or the hydroxyl group or amino group obtained on the surface by hydrolysis, are directly converted into their active esters in an inert organic solvent by CDI or TPG.

Of course, if the carboxyl group and the pro-carboxyl group on the surface of the micro/nano material have already been converted into active esters, they are directly used for subsequent covalent modification.

To realize the process of the present disclosure, it is necessary to separate the modified micro/nano material from the reaction mixtures. The micro/nano material as particles are suitable for separation by centrifugation or ultra-filtration, the centrifugation force required for separation is determined according to the density and volume of the particles, and the cut-off molecular weight of the ultrafiltration film used is determined according to the volume of the particles. The film with a large area or a large volume of attached solid is separated by mechanical operation, while the film with a too small area or a too small volume of attached solid is separated by centrifugation or ultrafiltration. It is also suitable to apply an external magnetic force to various shapes of magnetic materials for separation.

In this embodiment, the step b includes the following steps:

b1, for a micro/nano material having active esters on the surface, a hydrophilic compound or polymer containing the primary or/and secondary aliphatic amine is used as a modification agent to react with the active esters for covalent modification;

b2, for the covalently modified micro/nano material in step b1, the carboxyl groups and the pro-carboxyl groups on the surface are converted into active esters, indirectly or directly; the modification agent in step b1 containing the primary or/and the secondary aliphatic amine reacts with the active ester on the surface of the material at −20° C. to 40° C., and covalently modify the surface of the micro/nano material through the formation of amide bonds and regenerates the carboxyl group or its active ester; where the hydrophilic compound with a molecular weight of less than 500 Daltons or polymer with a molecular weight of 500 Daltons or more, containing the primary or/and secondary aliphatic amine, are used as the modification agent;

b3, steps b1 and b2 are repeated according to the desired number of covalently modified layers; where the step b3 is designed for a multilayer modification process and only needs to repeat b1 and b2 after active esters are repeatedly formed on the surface layer; the modification agents are selected to realize the multilayer covalent modification process so as to add the number of covalently modified layers of the selected modification agent until the desired multiple covalent modification layers are obtained for low non-specific adsorption.

In this embodiment, the method further includes the step of:

c. after the last covalent modification in step b, one or more of a carboxyl group, a pro-carboxyl group, a cation, an anion, a neutral hydrophilic functional group, an active ester, a chelating metal ion functional group and a protein disulfide selective modification functional group is obtained on the surface of the micro/nano material; where the metal ion chelating functional group is a chelate of $Ni^{2+}$ and $Cu^{2+}$ functional group; when the required number of layers has been achieved, the covalent modification is completed to form the desired functional group on the surface of the material for the last modification; of course, after the first layer modification has been performed according to the previous steps, a single layer-modified product is yielded without carboxylating the surface pro-carboxyl group.

In step c, when a protein disulfide selective modification functional group is obtained, the functional group will possess the following characteristics:

the protein-disulfide-selective modification group contains two reactive functional groups enabling Michael addition and/or nucleophilic substitution reaction with a sulfhydryl group, with no more than 10 covalent bonds located between the two reactive functional groups. The protein disulfide selective modification functional group may additionally contain a carboxyl group to form an amide bond with other components.

The reactive functional group undergoing Michael addition reaction with sulfhydryl group is an acryloyl group, or a vinyl sulfone group, i.e. $R^1$—CH=CH—$SO_2$—$R^2$, and such a reactive group when functioning alone, acts as a pro-carboxyl group; its reaction center is β position of carbonyl in acroleyl group and β olefin carbon atom of sulfonyl group.

The reactive group undergoing nucleophilic substitution reaction with a sulfhydryl group is alkyl containing one or more of chlorine, bromine, iodine, trifluoroacetate or p-toluenesulfonate at α-saturated carbon atom of a carbonyl group, a sulfone group, an olefin, or an aromatic ring, and a group from which the alkyl is derived after the Michael-addition of the protein sulfhydryl group, and such a reactive group acting alone is a pro-carboxyl group; chlorine, bromine, iodine, trifluoroacetate, and p-toluenesulfonate are the leaving group X of the nucleophilic substitution reaction, and the reaction center of the nucleophilic substitution is an α-saturated carbon atom corresponding to the carbonyl group, the sulfone group, the olefin and the aromatic ring.

In the protein-disulfide-selective modification group, the fragment linking two reaction centers of sulfhydryl groups does not contain a ring or a trialkyl substituent, and the two reaction centers of sulfhydryl groups should be simultaneously connected to the five- or six-membered ring used in the linking fragments. The carboxyl group contained in the protein-disulfide-selective modification group for covalently linking with the micro/nano material, is converted into an active ester, an acid anhydride or an acid chloride to react with the primary and secondary amine on the surface of the micro/nano material, so as to obtain the protein-disulfide-selective modification group on the surface of the modified micro/nano material.

When the protein-disulfide-selective modification group is used, the disulfide bond on the surface of the target protein is first reduced to two spatially adjacent free sulfhydryl groups by trialkylphosphine, and then such two spatially adjacent protein sulfhydryl groups simultaneously react with the two reaction centers in the protein-disulfide-selective modification group on the surface of the micro/nano material, thereby achieving site-selective covalent attachment/immobilization for the protein disulfide bond.

The application of the above protein-disulfide-selective modification group also has the following characteristics: the carboxyl group contained in the protein-disulfide-selective modification group is covalently linked to the polymer/small molecule amine group having no sulfhydryl groups and disulfide bonds on the surface, to obtain the protein-disulfide-selective modification group and thus a selective modification or labeling agent for disulfide bonds on protein surface; trialkylphosphine is used to reduce the surface disulfide bond of the protein to two adjacent free sulfhydryl groups, to simultaneously react with the two reactive groups in the protein-disulfide-selective modification group in the selective modification/labeling agent described above, and thereby achieving the site-specific covalent attachment or labeling.

In this embodiment, in step a, the active esters are derived from the carboxyl group or/and the pro-carboxyl group on the surface of the modified micro/nano material, and the generation method thereof includes the steps of: directly converting the carboxyl groups on the surface of the modified micro/nano material into active esters, or converting the pro-carboxyl group on the surface of the micro/nano material into the carboxyl groups and then into an active ester, or converting the pro-carboxyl group on the surface of the modified micro/nano material into the aliphatic hydroxyl groups and/or an aliphatic amine groups, and then into active esters by the reaction with CDI or TPG, or directly converting the pro-carboxyl groups on the surface of the modified micro/nano material into active esters; reacting such exposed active esters with a long linear amino acid to regain carboxyl groups, or reacting with a linear polyamine containing a plurality of primary aliphatic amines to form the aliphatic amine groups, which then reacts with a material containing the pro-carboxyl group and the active ester to regain the pro-carboxyl group and/or reacting with cyclic anhydride to regain the carboxyl group, so as to insert a linear linking arm between the carboxyl group or the pro-carboxyl group and the micro/nano material, and then converting the resulting surface carboxyl groups or pro-carboxyl groups into active esters.

In step b, the modification agent used herein includes A type modification agent and B type modification agent, and the molecular weight of both do not exceed 3000 Daltons.

The A type modification agent is a hydrophilic compound or polymer containing a primary or/and secondary aliphatic amine, and one or more of an N, N-dimethyl substituted aliphatic tertiary amine, N, N-diethyl substituted aliphatic tertiary amine and N, N-di-n-propyl substituted aliphatic tertiary amine. The A type modification agent is classified into A1 subtype modification agent and A2 subtype modification agent. Per molecule of the A1 subtype modification agent contains at least two primary and/or secondary aliphatic amines and at least one N,N-dialkyl substituted aliphatic tertiary amine functional groups. The A2 subtype modification agent contains only one primary or secondary aliphatic amine, but contains at least one N,N-dialkyl substituted aliphatic tertiary amine functional group.

The A1 subtype modification agent and the A2 subtype modification agent are used in step b as follows. The A1 subtype modification agent is used alone, or a mixture of the A1 subtype modification agent and the A2 subtype modification agent in any ratio is used. The sum of the molar amount of the primary and secondary aliphatic amines from the modification agent is in more than 10% excess to the molar amount of the active esters on the surface of the micro/nano material during modification. Unless the modification is to be finished, that is, the last layer of modification is to be formed, the A2 subtype modification agent is not used alone in step b.

The B type modification agent is a hydrophilic compound or polymer containing the primary or/and secondary aliphatic amine, but containing none of N, N-dimethyl substituted aliphatic tertiary amines, N, N-diethyl substituted aliphatic tertiary amines and N, N-di-n-propyl substituted aliphatic tertiary amines, and is classified into B1 subtype modification agent, B2 subtype modification agent, B3 subtype modification agent and B4 subtype modification agent.

The B1 subtype modification agent has a linear structure, with a primary or secondary aliphatic amine on one end, and an aliphatic carboxyl group or a pro-carboxyl group which is neither an amine nor a hydroxyl group on the other end. The B2 subtype modification agent has a linear structure, with primary and/or secondary aliphatic amines on both ends. The B3 subtype modification agent has a linear structure, with a primary or secondary aliphatic amine on one end, and a methoxy or ethoxy group on the other end. The B4 subtype modification agent has a non-linear structure containing at least two primary aliphatic amines and/or secondary aliphatic amines and an uncertain number of tertiary amines or amides. The B type modification agent includes dendrimers having the terminal primary aliphatic amines, chitosan, the amide derivatives of polymaleic anhydride and polyamine compound or polymer, polyethyleneimine, ethylenediamine-terminated polyethyleneimine, polypropyleneimine, propylenediamine-terminated polypropylene, proteins having an isoelectric point above 4.0.

In step b, the B1 subtype modification agent, B2 subtype modification agent or B4 subtype modification agent, or a mixture thereof in any ratio, is used. And the sum of molar amount of the primary and secondary aliphatic amines from the modification agent(s) is in more than 10% excess to the molar amount of the active esters on the surface of the micro/nano material. The B3 subtype modification agent regulates the ratio of the molar amount of the amine groups from the B1 subtype modification agent, the B2 subtype modification agent or the B4 subtype modification agent. Unless the modification is to be finished, that is, the last layer of covalent modification is to be formed, the B3 subtype modification agent is not used alone in step b.

For example, the last modification only uses the B1 subtype modification agent with one end being the aliphatic carboxyl group to directly obtain a carboxyl functional group; the last modification only uses the A2 subtype modification agent alone to directly obtain a tertiary amine from the modification agent as a weak cationic functional group; and the last modification only uses the B3 subtype modification agent to directly obtain a neutral hydrophilic surface from the modification agent.

In the last modification, as long as one of the B1 subtype with one end being a carboxyl group, the A2 subtype modification agent, and the B3 subtype modification agent, or a mixture thereof in any ratio, is used alone as the modification agent, the primary and secondary amine functional groups are directly obtained on the surface of the material as the weak cations in the aqueous solution. Such primary and secondary amines are further modified with a cyclic acid anhydride to obtain the carboxyl groups, or are modified with one of the active esters of haloacetic acid, O-Ts glycolic acid, glycidyl-succinic acid monoester, N-bromoacetyl-6-aminocaproate, N-trifluoroacetylglycine, 4-butyraldehyde acid, S-acetyl thioglycolate, or a mixture thereof in any ratio, to obtain the pro-carboxyl group.

In the last modification, as long as one of the B1 subtype with a carboxyl group at one end, the A2 subtype modification agent, and the B3 subtype modification agent or a mixture thereof in any ratio, is used alone as the modification agent, one of the active esters of haloacetic acid, N-bromoacetyl-6-aminocaproate, O-Ts glycolic acid, glycidyl-succinic acid monoester, N-trifluoroacetylglycine, 4-butyraldehyde acid, S-acetyl thioglycolate, or a mixture thereof in any ratio, is used to block the remaining amide groups, and then 1,3-propyl sultone is used for modification to obtain the amphoteric ion pairs and the pro-carboxyl groups from the active esters used for blocking the remaining amino groups on the surface, which are further converted into any desired functional groups.

In the last modification, as long as one of the B1 subtype with one end being a carboxyl group and the B3 subtype modification agent, or a mixture thereof in any ratio, is used alone as the modification agent, the methyl/ethyl/n-propyl trifluoromethanesulfonate or methyl iodide, or a mixture thereof in any ratio, is used alone in an inert organic solvent to modify the primary, secondary and tertiary amines on the surface to obtain the strong cationic groups.

In the last modification, as long as one of the B1 subtype with one end being a carboxyl group, the A2 subtype modification agent, and the B3 subtype modification agent, or a mixture thereof in any ratio, is used alone as the modification agent, primary/secondary aliphatic amines remaining on the surface are activated by CDI to carbonyl imidazole or activated by TPG to a mixed anhydride, and then modified with N,N-biscarboxymethyllysine or N-carboxymethylglycine to obtain the metal ion $Ni^{2+}$ and $Cu^{2+}$ chelating functional group. After the modification has been finished and the aliphatic carboxyl group has been formed on the surface of the micro/nano material using the required method, active esters are formed by using DCC plus one of NHS, SNHS or p-nitrophenol, and are further conjugated with N, N-biscarboxylatelysine or N-carboxymethylglycine in a neutral buffer containing no primary or secondary amine, also to obtain metal ions $Ni^{2+}$ and $Cu^{2+}$ chelating functional groups.

The A type modification agent and B type modification agent are mixed in step b as follows. The A and B type agents are mixed in any ratio. The sum of the molar amount of the primary and secondary aliphatic amines from the modification agents is in more than 10% excess to the molar amount of the active esters on the surface of the micro/nano material. Unless the modification is to be finished and the last layer of modification is to be formed, a mixture thereof in any ratio consisting only of the A2 subtype modification agent and the B3 subtype modification agent is not used in step b.

The representative structures of A1 subtype modification agent and A2 subtype modification agent are as follows.

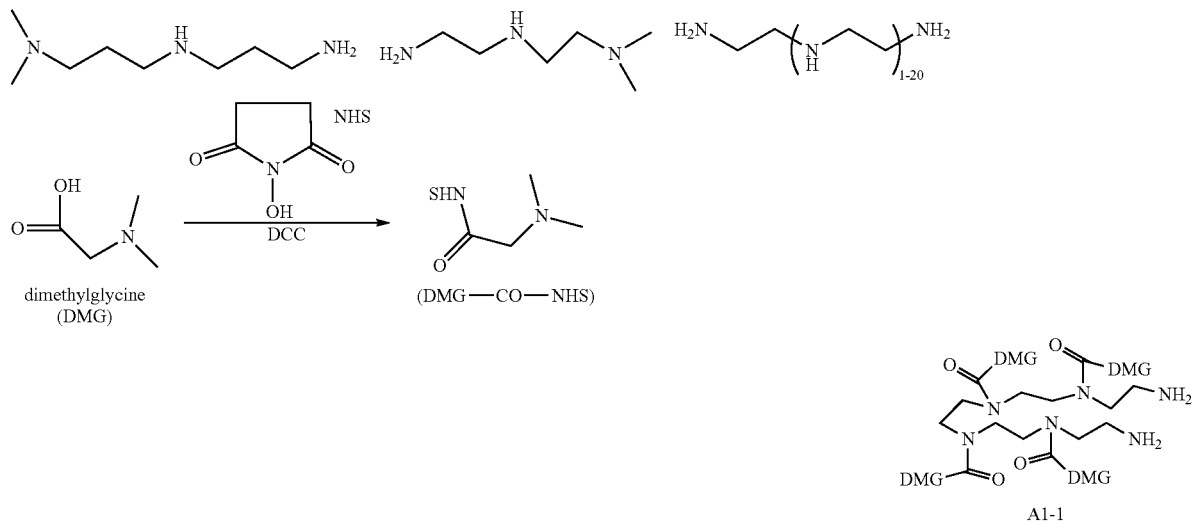

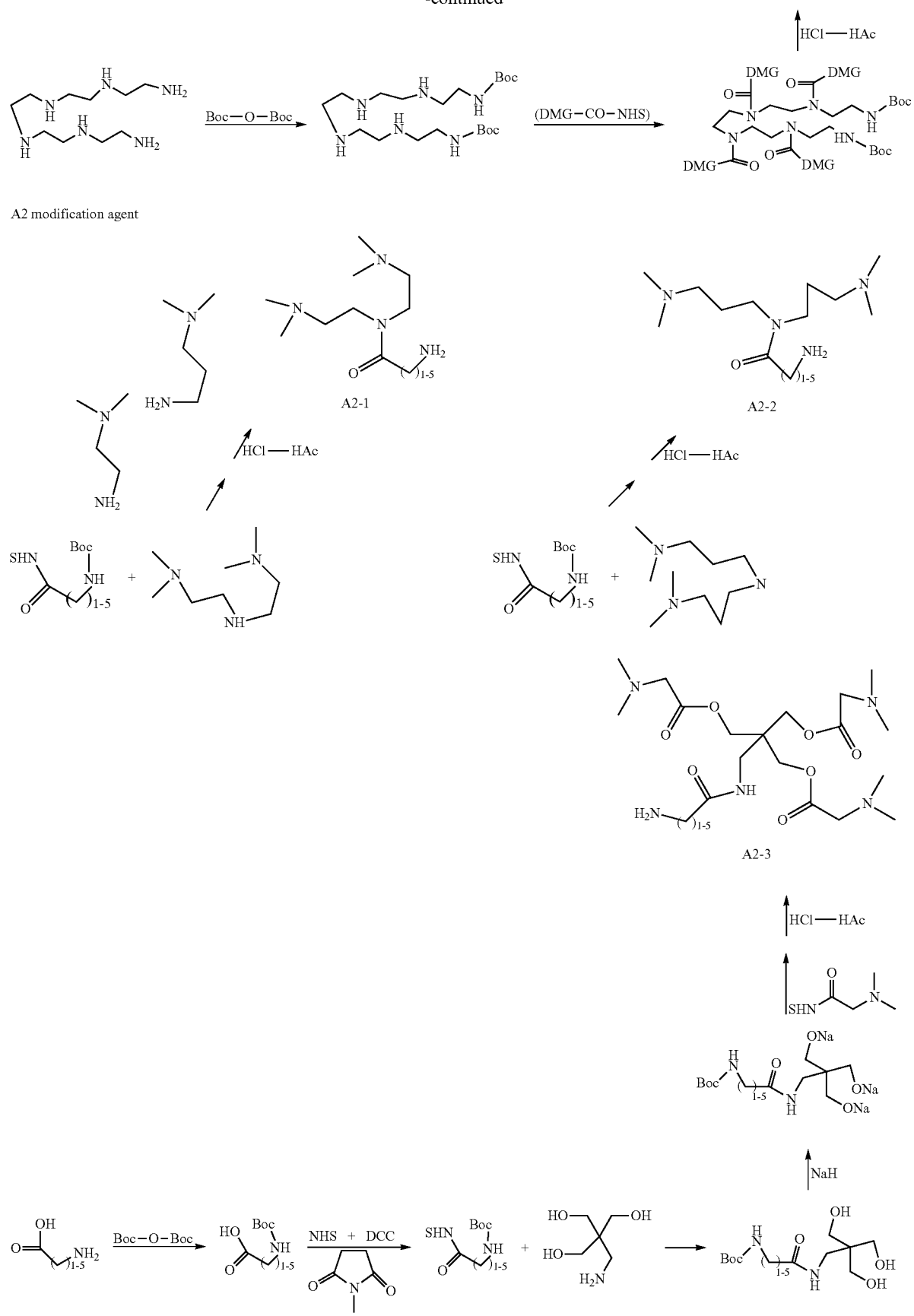

The representative structures of B1 subtype modification agent, B2 subtype modification agent and B3 subtype modification agent are as follows.

B1 modification agent

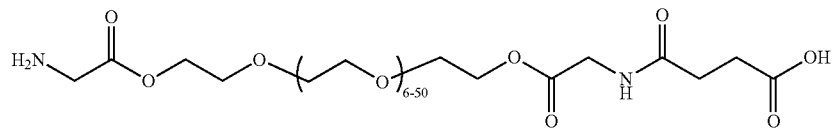

B1-1

B2 modification agent

B3 modification agent

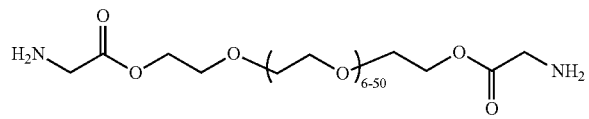

B2-1

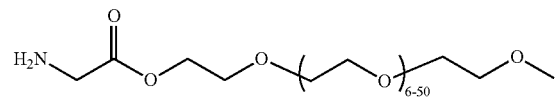

B3-1

In the embodiment, the A type modification agent further includes an A3 subtype modification agent, an A4 subtype modification agent, an A5 subtype modification agent and an A6 subtype modification agent.

The A3 subtype modification agent has an amphoteric ion pair in the chemical structure and contains at least two primary and/or secondary aliphatic amines which can react with the active esters, or contains only one primary or secondary aliphatic amine which can react with active esters and at least one carboxyl or pro-carboxyl group.

The A4 subtype modification agent has an amphoteric ion pair in the chemical structure, and contains only one primary or secondary aliphatic amine which can react with the active esters, but no desired carboxyl group or pro-carboxyl group. Unless the modification is to be finished, that is, the last layer of covalent modification is to be formed, the A4 subtype modification agent is not used alone in step b.

The primary and secondary aliphatic amines of the A1 subtype modification agent are protected by Boc; the tertiary amine group reacts with 1,3-propyl sultone to form zwitterion; and then Boc protecting group is removed to obtain the A3 subtype modification agent. The representative structure of the A3 subtype modification agent is as follows.

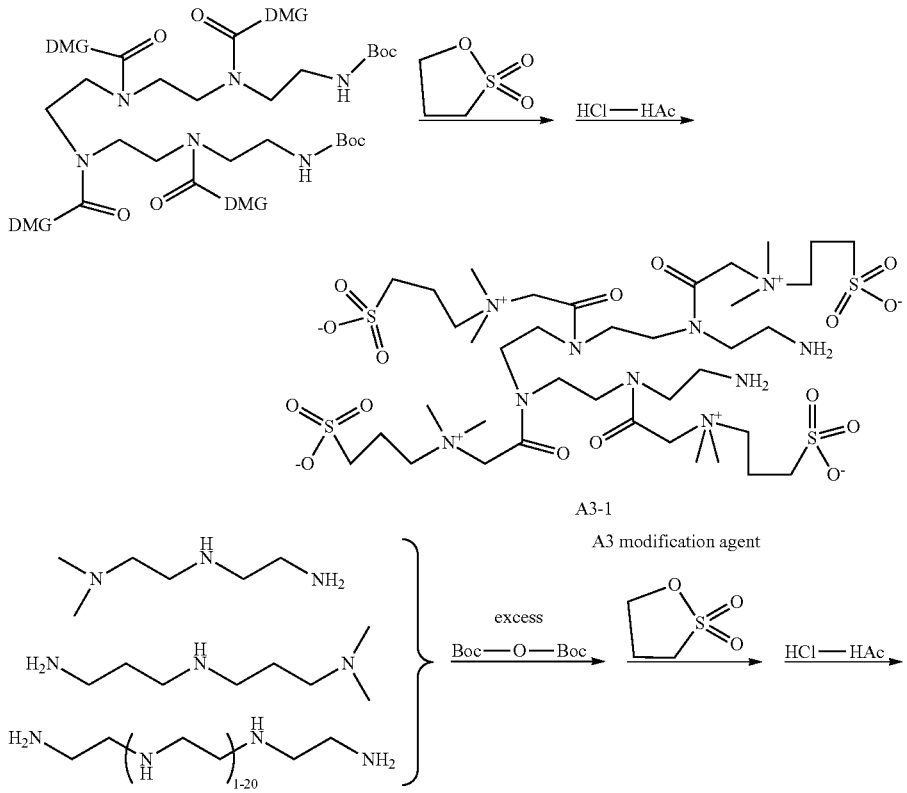

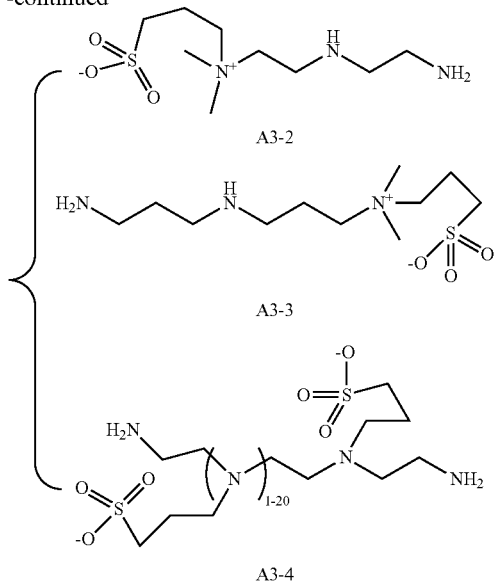
The primary and secondary aliphatic amine of the A2 subtype modification agent are protected by Boc; the tertiary amino group reacts with 1,3-propyl sultone to form a amphoteric ion, and then Boc protection is removed to obtain the A4 subtype modification agent. The representative structure of the A4 subtype modification agent is as follows.
A4 modification agent
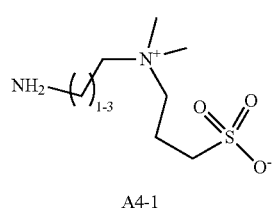
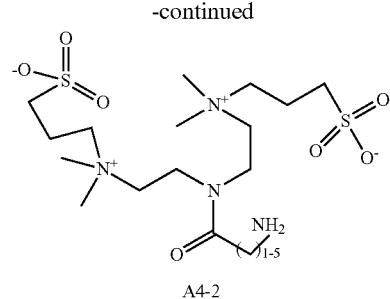
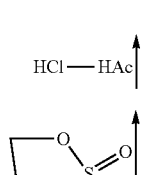
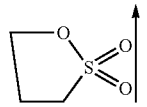
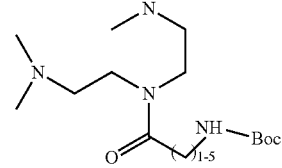
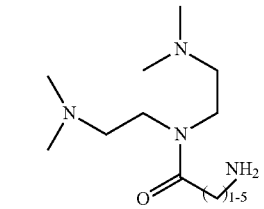

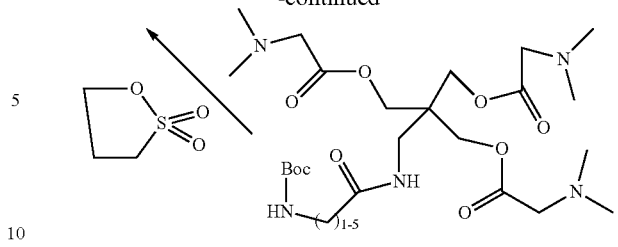

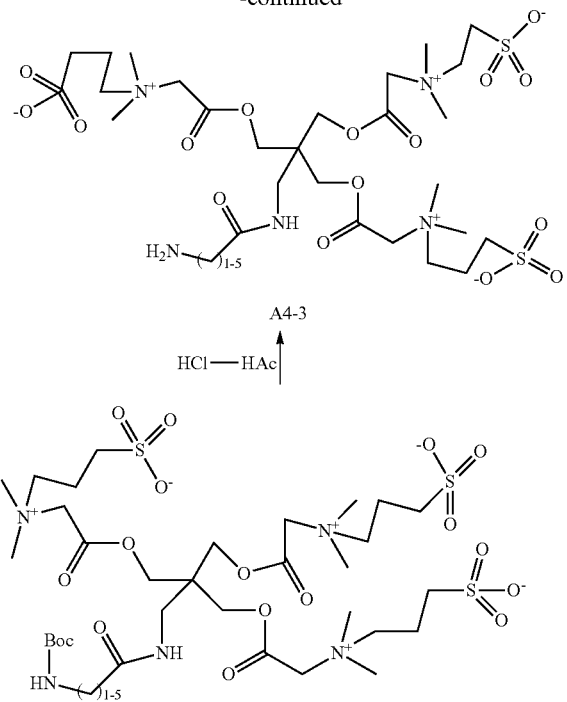

The A5 subtype modification agent is an anionic subtype modification agent and the A6 subtype modification agent is a cationic subtype modification agent. The A5 subtype modification agent has a single or multiple sulfonic acid and/or phosphate anions, and the A5 subtype modification agent containing one primary aliphatic amine is classified into A5-1, while the A5 subtype modification agent containing multiple primary aliphatic amines is classified into A5-2. The A6 subtype modification agent contains a single or multiple quaternary ammonium or tertiary amines, and the A6 subtype modification agent containing one primary aliphatic amine is classified into A6-1. The A6 subtype modification agent containing multiple primary aliphatic amines is classified into A6-2. The A5 and A6 subtype modification agents are used in pair for covalent modification to form the ion pair modification layer.

The representative structure of the A5 subtype modification agent is as follows.

A5-1 modification agent

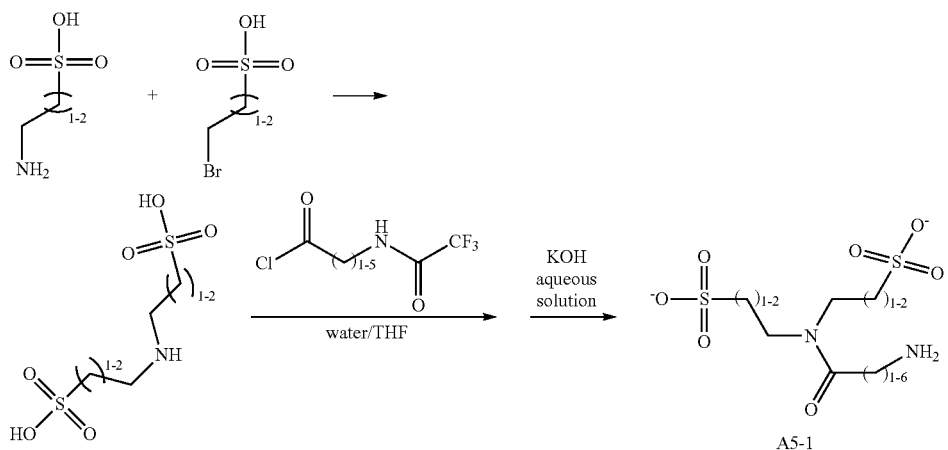

A5-2 modification agent

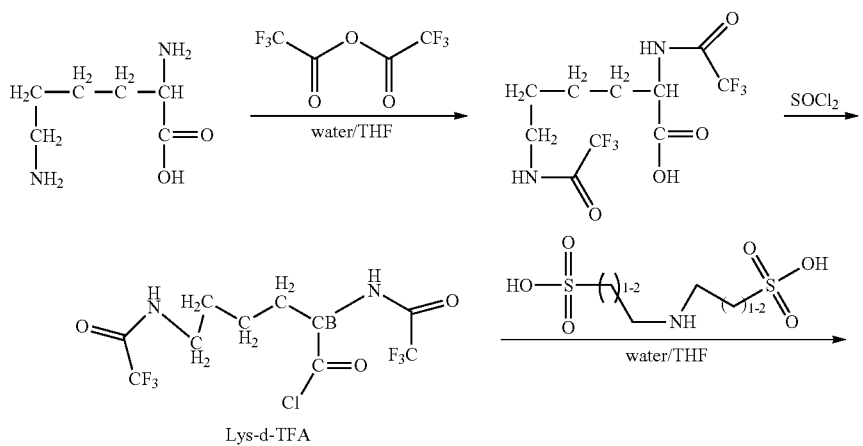

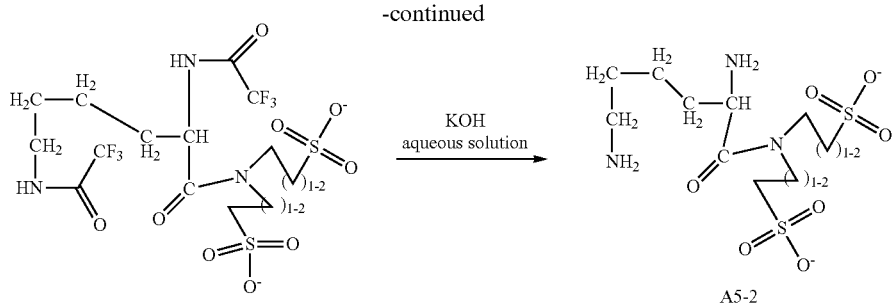
The representative structure of the A6 subtype modification agent is as follows.
A6-1 modification agent
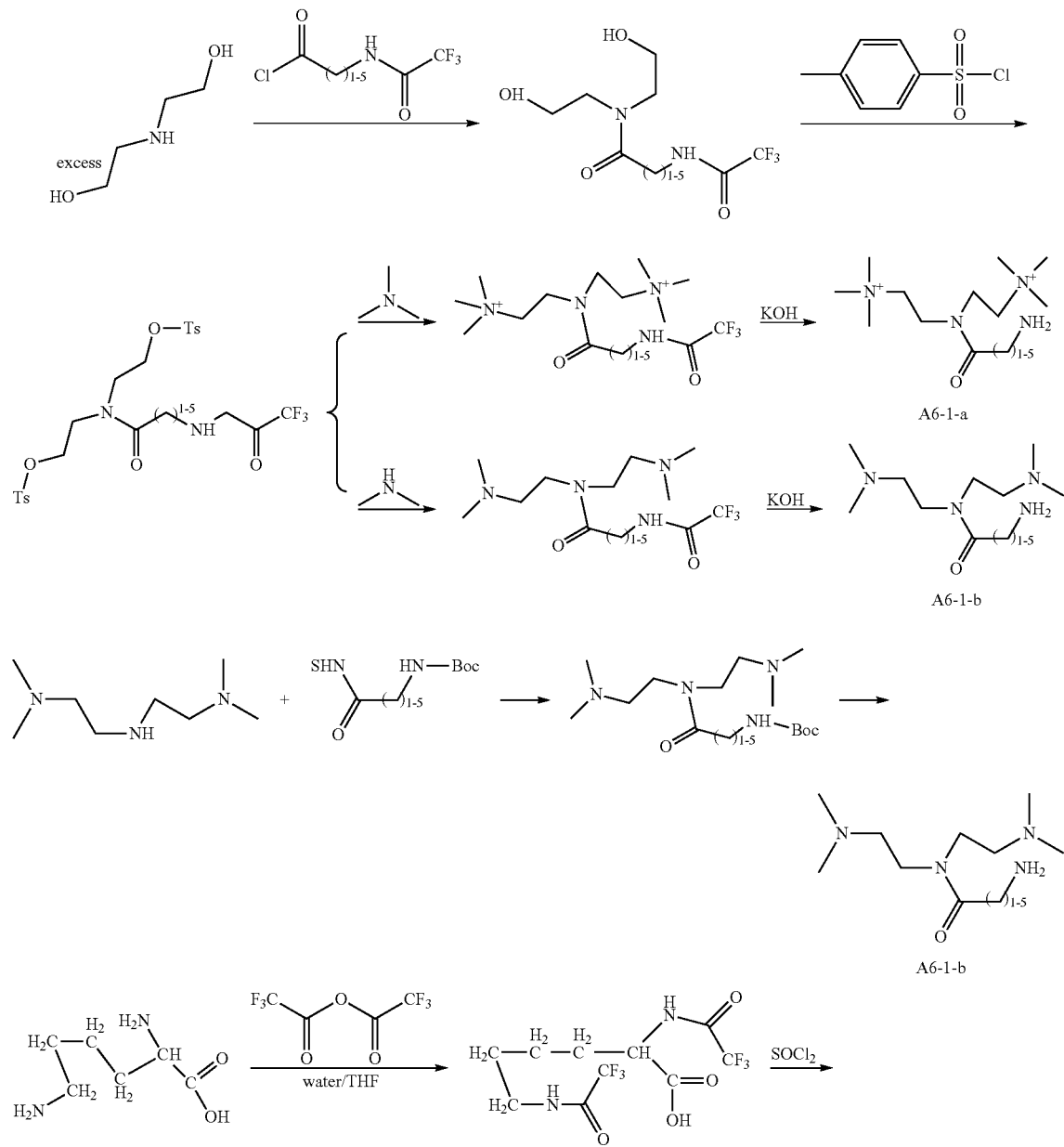

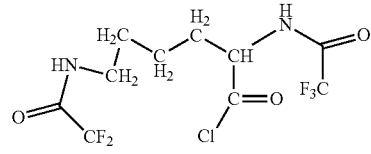

Lys-d-TFA

A6-2 modification agent

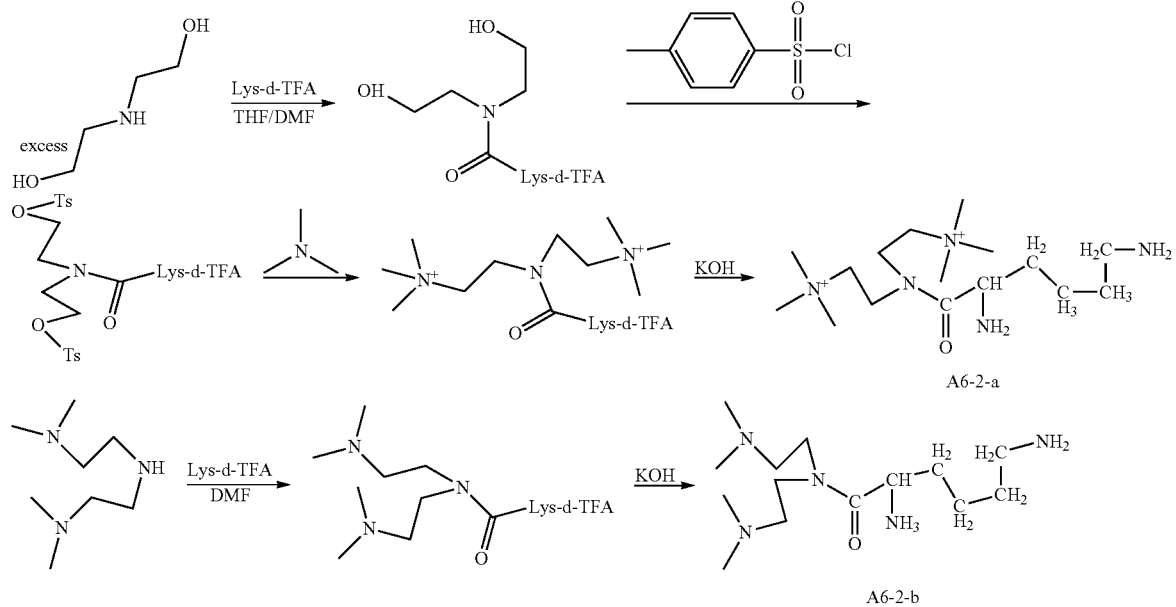

In step b, the A3 subtype modification agent is used alone, or mixed with any combination of A1 subtype modification agent, A2 subtype modification agent, A4 subtype modification agent, B1 subtype modification agent, B2 subtype modification agent and B3 subtype modification agent in any ratio. The ratio of the sum of the molar amount of A1, A3, B1 and B2 subtype modification agents in the mixture modification agent needs to be greater than 10%.

The A4 subtype modification agent is suitable for single use to obtain a surface modified with amphoteric ion pairs only in the last modification.

In step b, the A4 subtype modification agent is mixed with any combination of A1 subtype modification agent, A3 subtype modification agent, B1 subtype modification agent, B2 subtype modification agent and B4 subtype modification agent in any ratio. The ratio of the sum of the molar amount of the A1, A3, B1, B2 and B4 subtype modification agents in the mixture as the modification agent needs to be greater than 10%.

In step b, the A5 and A6 subtype modification agents are used in combination to form a mixture. In the mixture, sulfonic acid anions or/and phosphate anions from the A5 subtype modification agent and quaternary cations and tertiary amine cations from the A6 subtype modification agent are equivalent in molar amount. If the A5-2 and A6-2 subtype modification agent are not used, the A3 or B3 subtype modification agent with a ratio of the molar amount of 10% above is added.

During the modification, the micro/nano material with active esters on the surface is suspended in an aqueous solution of about pH 6.0, and reacts with the modification agent mixture added at room temperature for more than 10 minutes; or the modification agent is suspended in an inert organic solvent and reacts with the active esters on the surface of the composite material in a suspended state for 10 minutes or longer; or the composite material with the carboxyl group on the surface is suspended in an aqueous solution of about pH 6.0 and the carboxyl group is activated by EDC, after the excessive activator is removed, the modification agent mixture is added to perform suspension reaction for more than 10 minutes; and the pro-carboxyl groups are converted into the carboxyl groups or their active esters, or the covalent modification is to be finished.

In step b1, when any of the modification agents and mixtures thereof in any ratio are used and the active esters on the surface of the micro/nano material are derived from CDI or TPG, the modification agents and the material are suspended for reaction in an inert organic solvent or a neutral aqueous solution or a mixed solvent for modification for 10 minutes or longer. Otherwise, the modification agents and the material are suspended for reaction in an inert organic solvent for modification for 10 minutes or longer. The modified micro/nano material is separated from the mixture by centrifugation or ultra-filtration.

In step b1, unless the A2 subtype modification agent or B3 subtype modification agent is used alone or a mixture of these two subtype modification agents in any ratio is used, in an inert organic solvent, one of active esters of haloacetic acid, N-bromoacetyl-6-aminocaproate, O-Ts glycolic acid, glycidyl-succinic acid monoester, 4-butyraldehyde acid, S-acetyl thioglycolatethe and N-trifluoroacetylglycine, or a mixture thereof in any ratio, reacts with the primary and secondary aliphatic amines on the surface of the modified material to obtain pro-carboxyl groups. The molar amount of the active esters is in more than 10% excess to that of reactive amine groups on the surface of the micro/nano material, forming halogenated hydrocarbons, O-Ts esters, epoxy groups, or trifluoroacetamide groups as pro-carboxyl groups. The modified micro/nano material is separated by centrifugation or ultra-filtration.

In step b2, when A1 subtype modification agent or/and A2 subtype modification agent are used in the previous steps of the covalent modification process, in an inert organic solvent, one of the active esters of haloacetic acid, N-bromoacetyl-6-aminocaproate, O-Ts glycolic acid, glycidyl-succinic acid monoester, N-trifluoroacetylglycine, 4-butyraldehyde acid and S-acetyl thioglycolate, or a mixture thereof in any ratio, is used to block the primary and secondary aliphatic amines remaining on the surface of the micro/nano material, and then 1,3-propyl sulfonyl ester which is in more than 10% excess to the molar amount of the dialkyl-substituted tertiary amine on the surface of the modified material is used in an inert organic solvent, to convert the alkyl tertiary amines from A1 subtype modification agent and A2 subtype modification agent to the zwitterions bearing the quaternary ammonium adjacent to the sulfonic acid in the modification layer. The modified micro/nano material is separated by centrifugation, ultra-filtration or mechanical operation and the pro-carboxyl groups on the surface of the modified material are converted into the aliphatic carboxyl groups and further activated for covalent modification to form the next layer.

In step b2, when A1 or A2 subtype modification agent is not used in the previous steps of the covalent modification process, in an inert organic solvent, one of active esters of haloacetic acid, O-Ts hydroxyacetic acid, 4-butyraldehyde, glycidyl-succinic acid monoester, N-trifluoroacetylglycine, N-bromoacetyl-6-aminocaproic acid and S-acetylmercaptoacetic acid, or a mixture thereof in any ratio, is used to block the primary and secondary aliphatic amines remaining on the surface of the material. The pro-carboxyl groups on the surface of the material are converted into the aliphatic carboxyl groups and then activated, or CDI or TPG is used to react with such carboxyl groups to obtain the acid acyl imidazole or the mixed acid anhydride as the active ester.

In step c, during the previous covalent modification process, the B1 subtype modification agent having an aliphatic amine group at one end and a carboxyl group at the other end is used alone to directly obtain aliphatic carboxyl groups in the modification layer. When one of the B2 subtype modification agent and B4 subtype modification agent or a mixture thereof in any ratio is used alone, in an inert organic solvent, one of active esters of haloacetic acid ester, N-bromoacetyl-6-aminocaproic acid ester, O-Ts hydroxyacetic acid ester, glycidyl-succinic acid ester, N-trifluoroacetylglycine ester, S-acetylmercaptoacetic acid ester and 4-butyraldehyde acid ester, or a mixture thereof in any ratio, is used to react with the primary and secondary aliphatic amines on the surface of the modified material, with the molar amount of the active esters in more than 10% excess to the molar amount of the reactive amine groups on the surface of the micro/nano material, forming one of the hydrocarbon, Ts ester, epoxy, trifluoroacetamide, aldehyde, and protected thiol or a mixture thereof.

In step c, in the previous covalent modification process: the A2 subtype modification agent is used alone to obtain the cationic surface functional groups of the alkyl-substituted tertiary amines, and the alkyl-substituted tertiary amines can be converted into the amphoteric ions as the surface functional groups with the quaternary ammonium adjacent to the sulfonic acid with an excess of 1,3-propyl sultone; and the B3 subtype modification agent is used alone to obtain a neutral and inert hydrophilic surface functional group.

In this embodiment, prior to the step a, the polymerization reaction and the monomer characteristics used to prepare the micro/nano material are as follows.

I. In the microemulsion system, the micro/nanomaterial is prepared by free radical polymerization, and has the following characteristics.

When using water-in-oil or W/O microemulsion system, special organic monomers and cross-linking agents include but are not limited to: acrylic acid, sodium cinnamate, N-acryloylethanolamine, N-methylol acrylamide, N-acryloylserine, N-acryloyl glutamic acid, N,N-bisacrylyl lysine, and derivatives of the described various hydrophilic modification agents after reacting with active esters of acrylic acid, maleic anhydride, allyl bromide, allyl Ts ester, N-maleylethanolamine, N-bromoacetyl-N'-maleylethylenediamine.

These special organic monomers are suitable for use alone or being mixed in any ratio, which however requires that the total concentration of polymerizable double bonds of the polymerization system from special organic monomers and cross-linking arms is above 0.1 mol/L in the polymerization phase. When the solubility of these special organic monomers and cross-linking arms is insufficient in the dispersed polymerization phase, zwitterions are introduced into the covalent structure thereof to meet the solubility requirements.

When using water-in-oil or O/W microemulsion system, special organic monomers and cross-linking agents include, but are not limited to, phenylpropenol, cinnamic acid, phenylpropenylamine, N-linoleoylserine, N-linoleylethanolamine, N,N'-bis linoleoyl lysine acid, N,N'-bisacryloyloctanediamine, 3-n-octanoyloxy-cinnamic acid, N,N'-double cinnamyl-1,8-octanediamine, 3-linoleoyloxycinnamic acid; these special organic monomers and cross-linking arms are used alone or mixed in any ratio, and the concentration of the polymerizable double bonds from specific organic monomers and cross-linking agent of the polymerization system is above 0.1 mol/L. A long hydrocarbon chain is introduced in the covalent structure of the special organic monomers and the cross-linking agent to increase the lipid solubility thereof to satisfy the solubility requirements in the dispersed phase.

When the polymerization is initiated by peroxide cracking, the monomers, the cross-linking agents and the initiators are mixed in a selected ratio with the micro/nano particles when required in the corresponding solvent, and dispersed in the microemulsion system. And then the catalyst solution is dispersed into the monomer phase of the microemulsion system followed by heating to accelerate the polymerization reaction. When an azo initiator is used, the operation is similar as in the case of a peroxide initiator, or all the materials including the catalyst required for the polymerization are thoroughly mixed and dispersed at 30° C. or less into the microemulsion system, and then the temperature is raised to initiate polymerization reaction.

II. The micro/nano material is prepared by a nucleophilic substitution reaction in a microemulsion system, and has the following characteristics.

The cross-linking agent has two types: multiple nucleophilic groups and multiple leaving groups. One or two types of cross-linking agents may be used for polymerization. Epoxy chloropropane is suitable as both a monomer and a cross-linking agent.

When using W/O microemulsion is used, special organic monomers and cross-linking arms providing multiple nucleophilic groups include, but are not limited to: lysine and ornithine, and various types of the modification agents containing multiple primary and/or secondary amines. Specific organic monomers and cross-linking agents providing multiple leaving groups, include N,N-dibromoacetyl lysine, N,N-dibromoacetylornithine, and the reaction derivatives of various types of modification agents containing multiple primary and/or secondary aliphatic amines with an excess of the active esters of haloacetic acid, O-Ts glycolic acid, and/or glycidol succinic anhydride monoester. Amphoteric ions are introduced into such special organic monomers and cross-linking agents to increase their water solubility to meet the solubility requirements in the dispersed phase thereof. These special organic monomers are used alone or mixed in any ratio in the polymerization system, but the total concentration of the functional group of the polymerization reaction from special organic monomers and cross-linking agents in the polymerization system is required to be above 0.1 mol/L. The representative structures and preparation diagrams of special organic monomers and cross-linking agents are as follows.

monomer for nucleophilic substitution reaction polymerization in aqueous phase

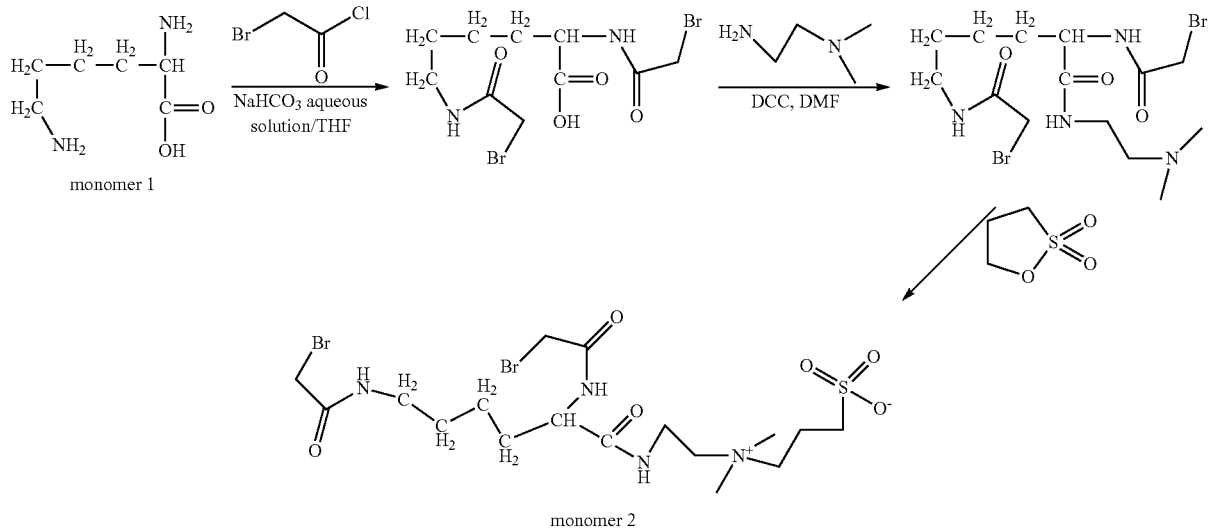

cross-linking agent for nucleophilic substitution reaction polymerization in aqueous phase

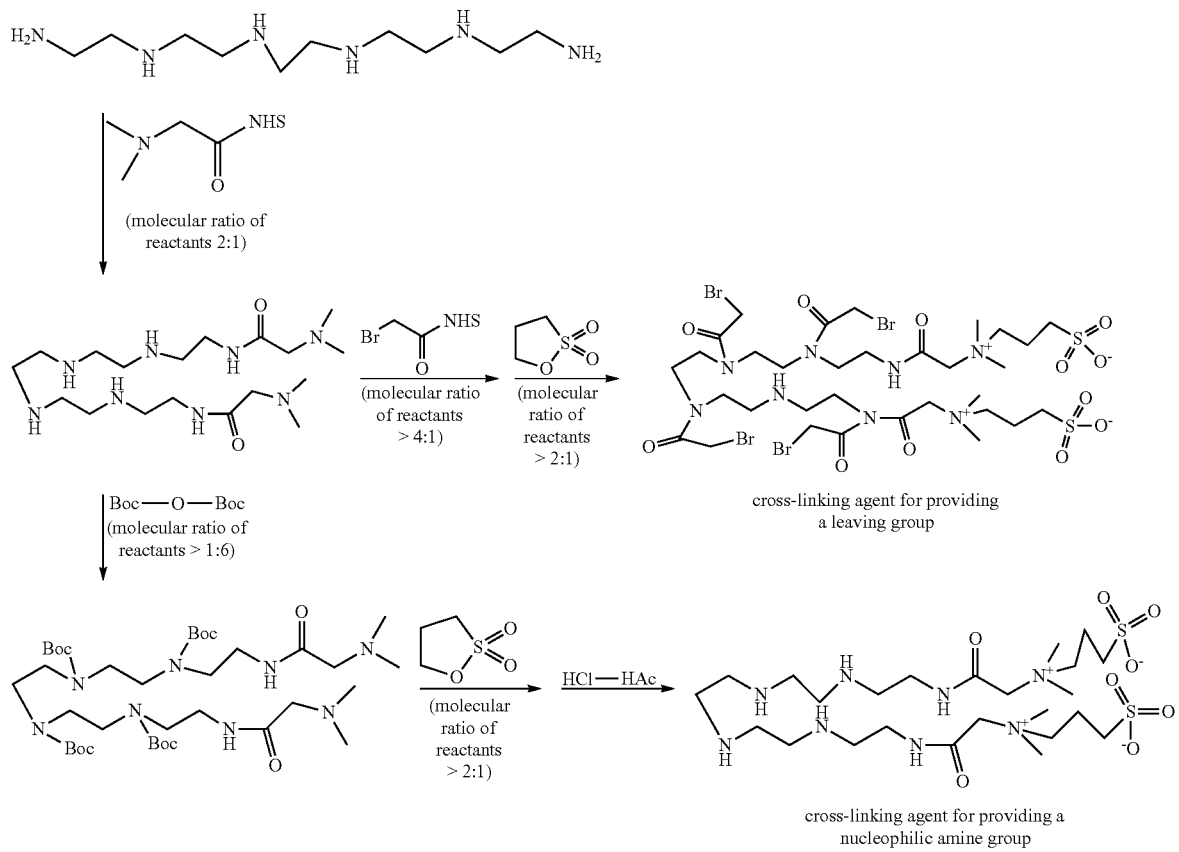

When O/W microemulsion is used, the monomers and cross-linking arms include, but are not limited to: N,N'-dibromoacetyl-4-hydroxy-1,8-octanediamine, epichlorohydrin, 4-hydroxy-1,8-octanediamine, bis-p-toluene sulfonate, and long hydrocarbon chains are introduced into those desired monomers and cross-linking agents to increase their lipid solubility. The monomers are suitable for being used alone or mixed in any ratio in polymerization. The representative structures and the schematic diagrams of the preparation routes of special organic monomers and cross-linking arms are as follows.

nanoparticles added when needed, and are dispersed into the microemulsion system. A weak base such as $NaCO_3$ aqueous solution is added to the W/O microemulsion, or an organic base like tri-n-butylamine is added to O/W microemulsion and dispersed into the microemulsion system, and the polymerization continues at room temperature for more than one hour to obtain the micro/nano material for modification.

III. The microemulsion system is used and undergoes polycondensation by amides, or polymerization of isocyanate or isothiocyanate, and has the following characteristics.

monomer for nucleophilic substitution reaction polymerization in oil phase

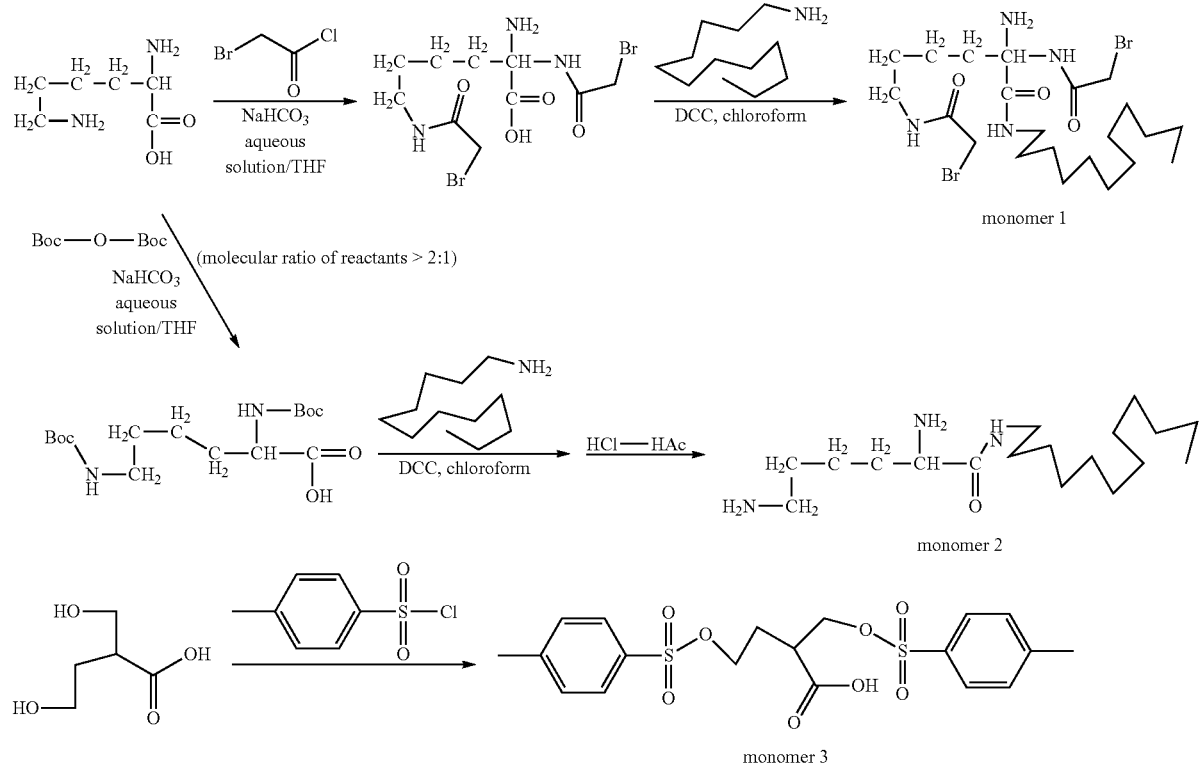

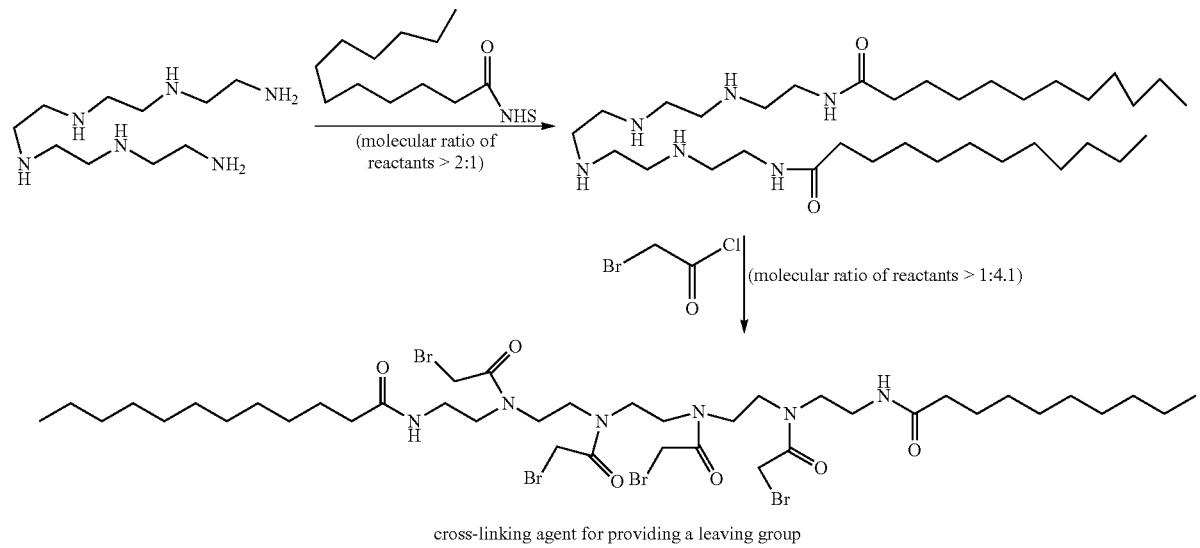

cross-linking agent for providing a leaving group

During polymerization, the monomers and the cross-linking agents are mixed in the selected ratios, with micro/

During the amide polycondensation reaction in W/O microemulsion, the special organic monomers and the cross-linking agents include but are not limited to aspartic acid, serine, 1,4-diamino-2-butanol, 1,4-diamino-2-butyric acid, valley acid, lysine, ornithine, polymaleic anhydride. Pro-carboxyl groups in such special organic monomers are the same as the pro-carboxyl groups in hydrophilic modification agents, and their solubility in water can easily meet the requirements. The selected special organic monomers are mixed uniformly and dispersed into the micro water phase of W/O, and an EDC aqueous solution is added to promote the polycondensation by amide to obtain the micro/nano material.

During the polycondensation with amide in O/W microemulsion, the special organic monomers and the cross-linking arms include but are not limited to: N-stearoyl lysine, 4-hydroxy-1,8-octanedioic acid, 4-hydroxy-1,8-octanediamine, N-stearoyl glutamic acid, their solubility in the oil phase can meet the requirement of total concentration of the polymerization functional groups. The pro-carboxyl functional groups in the special organic monomers and the cross-linking agents include the alkyl primary alcohol trifluoroacetate, the aliphatic carboxylic acid p-nitrophenol ester. After the selected monomers are mixed, DCC is added to promote the formation of amides through the dehydration and obtain the micro/nano material through polycondensation.

During the polymerization reaction of polyisocyanate monomers in the O/W microemulsion, 1,7-dihydroxy-4-(N-bromoacetyl)-heptylamine and trimethylol-(6-(N-bromoacetyl)-aminohexanoyl)-aminomethane are representatives of polyhydroxy monomers, and 1,4-phenylene diisocyanate is a representative of polyisocyanate-containing monomers. Trifluoroacetate and fatty acid p-nitrophenolate are suitable as pro-carboxyl groups in the special organic monomers. The special organic monomers except for the polyisocyanate are firstly mixed, and a polyisocyanate is dispersed into the microemulsion system to initiate the reaction and obtain the micro/nano material.

During the polymerization of polyisocyanate monomers in the O/W microemulsion, 1,8-octanediamine, 4-hydroxy-1,8-octanediamine, and 1,7-heptanediamine are representatives of polyamine monomers and 1,4-phenyl diisothiocyanate is a representative of polyisothiocyanate-containing monomers. Trifluoroacetate esters of monomers and fatty acid p-nitrophenol esters are suitable to provide pro-carboxyl groups in special monomers. Monomers other than the polyisothiocyanate are firstly mixed, and the polyisothiocyanate is dispersed into the microemulsion system to initiate the reaction for the micro/nano material.

IV. When preparing the micro/nano film, the monomer mixture used is transferred to an indented container or a surface having a solid of a desired shape, and the polymerization is initiated and accelerated in a similar manner to the preparation of the micro/nano particles.

In the present disclosure, when the micro/nano material is prepared by a polymerization reaction, suitable polymerization reactions and monomers have the following characteristics.

(I) A micro/nano core for preparing the composite micro/nano material, includes magnetic nanoparticles, quantum dots, up-conversion luminescent particles, metal nanoparticles, organic fluorescent particles insoluble in water or a hydrocarbon solvent, or a mixture of the above particles. These micro/nano cores are compatible with the polymerization used, i.e., the desired properties of the micro/nano cores after polymerization remain. The monomers used in this type of polymerization have the following characteristics.

(1) In addition to the radical polymerization, the monomers used in the polymerization reaction contain not less than two functional groups for the polymerization reaction.

(2) The total amount of the specific organic monomers contained in the polymerization reaction system used has a molar ratio of not less than 1% among the monomers, and the solubility of each special organic monomer in the corresponding dispersed phase is greater than 0.010 mmol/L.

(II) When preparing the micro/nano film to which the multi-layer covalent modification method is applied, the same monomers and ratio for making the micro/nano particles are used, the mixture to be polymerized is spread to the inner depressed solid surface or within the container to form a thin layer, and then initiate the polymerization reaction.

In this embodiment, after the modification is completed, a protein disulfide selective modification functional group is formed on the surface of the micro/nano material, and a disulfide bond on the protein is reduced under neutral conditions by using trialkylphosphine to two adjacent reactive sulfhydryl groups, for reaction with two adjacent reactive groups in the protein disulfide selective modification functional group, to achieve site selective immobilization on the disulfide bond on the surface of the protein.

The representative structure of the protein disulfide selective modification functional group is as follows.

(1) A short linear linking fragment is present between two reactive groups required for the protein disulfide selective modification functional group: the spacing is ≤10 bonds.

protein disulfide selective modification functional group: short linear linking fragment beween two active groups, n+1 ± 7; m is not limited.

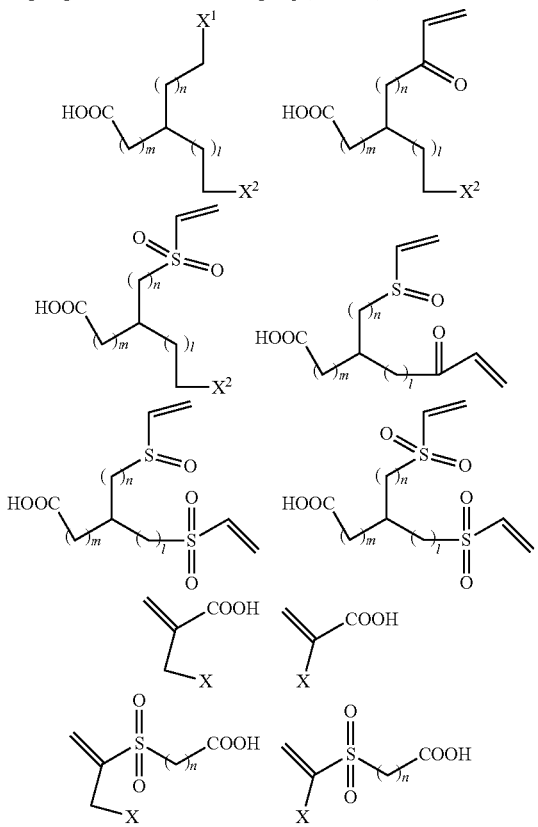

(2) A flexible ring linking fragment is present between two active groups required by the protein disulfide selective modification functional group: the spacing is ≤10 bonds.

protein disulfide selective modification functional group: flexible ring linking fragment between two active groups protein disulfide selective modification functional group: aromatic ring linking fragment between two active groups

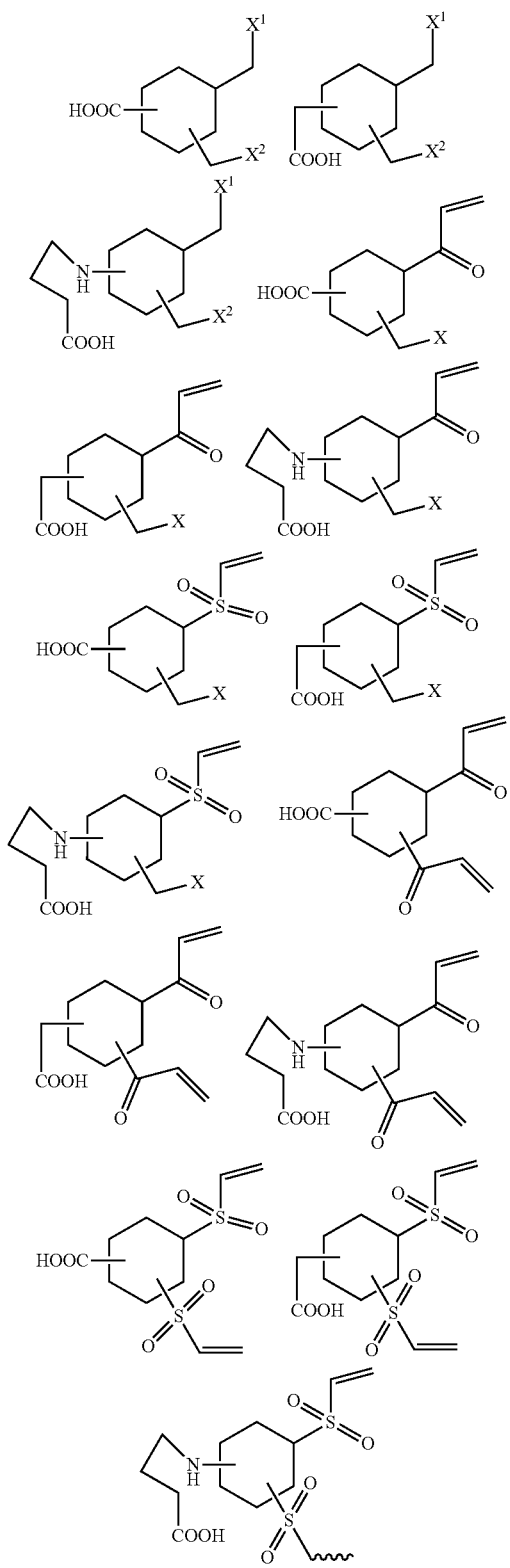
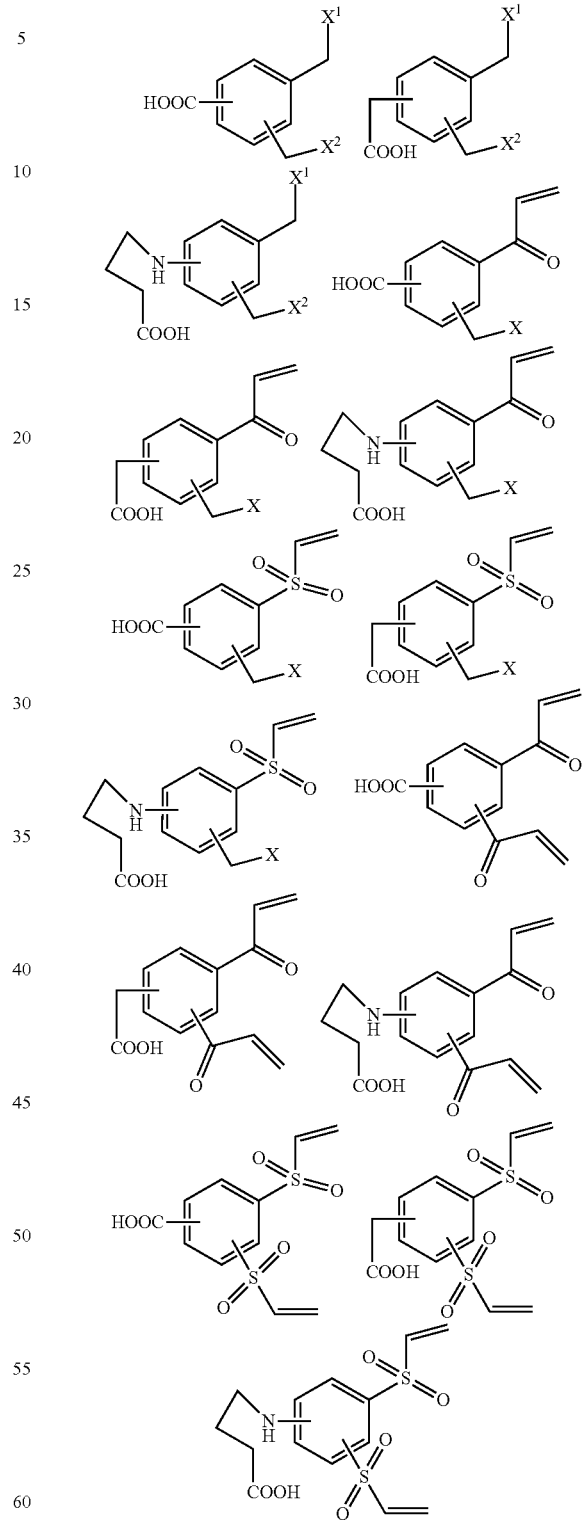

(3) An aromatic linking fragment is present between two active groups required by the protein disulfide selective modification functional group: the spacing is ≤10 bonds.

In addition, the carboxyl group, in the protein disulfide selective modification functional group, is covalently bonded to the amine group of a small molecule or macromolecule/polymer containing neither sulfhydryl groups nor disulfide bonds on the surface, and the conjugate of the protein disulfide selective modification functional group and the small molecule or macromolecule/polymer is used as a protein disulfide-selective modification agent/labelling agent. In application, the disulfide bond on a protein is reduced to a pair of free sulfhydryl groups by trialkylphosphine under neutral conditions, which are thus selectively modified, labelled or covalently conjugated by the conjugate of the protein disulfide selective modification functional group and the small molecule or macromolecule/polymer according to the site of the disulfide bond on the surface of the protein. The macromolecular polymers having no sulfhydryl group and disulfide bond on the surface include proteins, nucleic acids, peptide nucleic acids, and polysaccharides.

In the embodiments, magnetic submicron particles (MSP) are used below as micro/nano materials to demonstrate the beneficial effects and the application of the present disclosure.

JSR-MSP—COOH is 1.5 μm carboxyl MSP from JSR Co., Ltd. (Shanghai, China); Bangs-MSP—COOH is 1.0 μm carboxyl MSP supplied by Bangs Laboratories Inc; Dynal-MSP—COOH is 1.0 μm carboxyl MSP supplied by Thermo-Fisher. A representative implementation process for carrying out the present disclosure is as follows.

Method 1 Production of MSP

In order to facilitate the demonstration of the effectiveness of the modification scheme of the present disclosure, MSP prepared in a W/O microemulsion system is used as the representative of the micro/nano material. For details on the preparation of magnetic fluid, microemulsion system and MSP in the W/O microemulsion system, please refer to the China Patent ZL201210046309.5 for details (date of patent, Sep. 24, 2014).

N-methylol acrylamide was used as a monomer, methylidene bisacrylamide was used as a cross-linking agent, potassium peroxydisulfate was used as an initiator, and tetramethylethylenediamine was used as a catalyst. MSP making process operation refers to the ZL201210046309.5 for details, W/O microemulsion system for aqueous phase free radical polymerization yielded MSP, N-methylol acrylamide in aqueous phase concentration of 0.4 kg/L, and the hydroxyl group from N-methylol acrylamide was a pro-carboxyl group. See Example 7 for details. For the obtained MSP, non-specific adsorption of 200 mg of a soluble protein per g of MSP was determined (see Method 2), and the non-specific adsorption of *Pseudomonas aeruginosa* aromatic sulfatase (PAAS) was 28%, and the non-specific adsorption of *Escherichia coli* alkaline phosphatase (ECAP) achieved 56%.

Method 2 Determination of Non-Specific Adsorption of Water-Soluble Protein on MSP ECAP was from Beijing Biotrand Biotechnology Co., Ltd. *Pseudomonas aeruginosa* aromatic sulfatase (PAAS, GenBank GI: 879288) was inserted into pET24a plasmid, with 6His tag added at the N-terminus for inducing expression in *E. coli* BL21 (DE3) and Ni2+-NTA (Beijing Biotrand Biotechnology Co., Ltd.) purification. Both enzymes were assayed with 1.0 mol/L Tris-HCl buffer (pH 10.0) at room temperature. 10.0 mM 4-nitrophenyl phosphate was used as an ECAP substrate while 5.0 mM 4-Nitrophenyl sulfate was used as a PAAS substrate. The absorbance was measured at 405 nm. The release of one micromole of product by enzyme action per minute was defined as one unit. ECAP and PAAS had specific activities of 1200 kU/g and 25 kU/g, respectively.

MSP was separated with PolyATract® System 1000 Stand magnetic separator (Promega, Madison, Wis., USA). For the non-specific adsorption, 5.0 μg of enzyme and 25 μg of MSP were mixed in a 1.50 mL Ependorf tube containing 0.20 mL of 20 mM Tris-HCl buffer (pH 8.0) for adsorption for 30 min. MSP was magnetically separated and gently washed twice with the above adsorption buffer. MSP was diluted, and 20 μL of the diluted sample was transferred to a 1.50 mL Ependorf tube followed by a magnetic separation to remove the supernatant. 1.0 mL of the chromogenic substrate at the final concentration was added, and the mixture was gently shaken at room temperature (about 22° C.) for 30 minutes, and then was magnetically separated for 1.0 min to remove MSP. 190 μL of the resulting product was quickly added with 10 μL of 10 M NaOH solution freshly prepared to terminate the reaction followed by measuring the absorption with 96-well plate and a Biotek ELX 800 plate reader. The activity was expressed by the increase in product absorption after reacting for 30 min.

Method 3 Non-Specific Adsorption of Small Hydrophobic Molecules by MSP

The non-specific adsorption of small molecule compounds was determined by using 4-nitro-1-naphthol benzoate as a model (Log P was +3.97 and was conveniently determined by a reverse phase HPLC-UV). 4-Nitro-1-naphthol benzoate was prepared through the reaction of 4-nitro-1-naphthol and benzoyl chloride. The resulting product was purified using a silica gel column, and until no impurities were detected in the product at 240 nm by a reverse phase HPLC, the non-specific adsorption of 25 μg of MSP to 16 and 64 μM of 4-nitro-1-naphthol benzoate was determined in 10.0 mM sodium phosphate buffer (pH 7.4).

The operation was described in the publication (Facile one-step coating approach to magnetic submicron particles with poly (ethylene glycol) coats and abundant accessible carboxyl groups. Int J NanoMed, 2013, 8: 791-807). The adsorption reaction was performed for 30 min, and the MSP was magnetically separated and washed once with the adsorption buffer followed by dissolving in tetrahydrofuran. 4-Nitro-1-naphthol benzoate was determined using an Agilent-1100 HPLC system equipped with an Elite ODS2 C18 column (4.6×250 mm, 5 μm). A mixture of 90% methanol and water was used as a mobile phase and the flow rate was set at 0.8 ml/min. The injection volume was 20 μL and the column temperature was maintained at 25° C. The detection wavelength was 335 nm.

Method 4. Determination of Carboxyl Active Ester on the Surface of Magnetic Particles 1-naphthylethylenediamine was used as a probe and the concentration of its aqueous solution was corrected by the adsorptivity of 5.0 $(mM)^{-1} \cdot cm^{-1}$ at 325 nm. The carboxyl groups on the surface of the MSP were converted into active esters by DCC and NHS in an inert organic solvent or in an HEPS buffer plus EDC and NHS at pH 6.0. 0.10 mg of the activated MSP was transferred into the HEPES buffer and the solvent was removed by magnetic separation. Then 0.40 mL of 0.10 mM 1-naphthylethylenediamine solution dissolved in the same solvent was added followed by mixing for 4 hours at room temperature. The supernatant was transferred and diluted 20 times, and fluorescence signal (excitation 330 nm, emission 430 nm) of the 1-naphthylethylenediamine was determined. The amount of 1-naphthylethylenediamine immobilized on the surface of MSP was calculated through the decrease in the amount of probe. With 1-naphediethylenediamine, the amount of non-specific adsorption on the un-activated MSP was determined by the solvent used to activate the carboxyl group. For deducting the non-specific adsorption of 1-naphthylethylenediamine, the amount of active ester on the surface of MSP was converted by a 1:1 molar ratio.

Example 1 Production of a Representative of A1-1 Modification Agent 1-1. The synthesis of the active ester of N,N-dimethylglycine was as follows. Dimethylglycine (DMG) was saturated in tetrahydrofuran (THF), NHS and DCC (the molar ratio of the three being 1:1:1) were also added, and stirred at room temperature for reacting overnight. The precipitate was filtered off, and the supernatant was concentrated 20 times using vacuum concentration. Diethyl ether was added to collect the precipitate for dissolution in a minimum volume of hot THF followed by another addition of diethyl ether to collect a precipitate as the active ester of N,N-dimethylglycine (DMG-CO—NHS).

1-2. The synthesis of pentaethylene hexamine bis-Boc protected primary amine was as follows. Pentaethylene hexamine was saturatedly dissolved in dimethylformamide (DMF), and di-tert-butyl pyrocarbonate (Boc-O-Boc) was added in a molar amount of twice that of pentaethylene hexamine and stirred for a reaction in 60 min at room temperature. Diethyl ether was added to collect the precipitate, which was then dissolved in a minimum amount of DMF followed by another addition of diethyl ether to collect the precipitate, and that is the pentaethylenehexamine bearing two Boc at two primary amines.

1-3. Bis-Boc protected pentaethylene hexamine was reacted with the active ester of N,N-dimethylglycine as follows. Bis-Boc protected pentaethylene hexamine was dissolved in DMF for saturation, and the active ester of the N,N-dimethylglycine saturated in THF (1:4.1) was added followed by a stirring for a reaction of 120 min at room temperature. Diethyl ether was added to collect the precipitate, which was dissolved in a minimum amount of hot DMF, and cooled to room temperature. Then, diethyl ether was added again to collect the precipitate to obtain 1,16-bis-Boc-4,7,10, 13-tetra-(N,N-dimethylglycyl)-pentaethylene hexamine.

1-4. Preparation of the A1-1 modification agent was as follows. 1,16-bis Boc-4,7,10,13-tetra-(N,N-dimethylglycyl)-pentaethylenehexamine was dissolved in an acetic acid solution containing 1.0 M HCl, and was stirred for reaction for 2 hours at room temperature. Finally, 10 M NaOH solution was added until a large amount of precipitate was yielded. The collected precipitate was dissolved in a minimum amount of 1.0 M HCl solution, and 10 M NaOH solution was added until a large amount of precipitate was obtained. After repeating the process of dissolving in acid and precipitating with alkaline three times, the target compound, A1-1 modification agent, was obtained. See FIG. 1 for the reaction route.

Example 2 Preparation of the Representatives of A2-3 Modification Agent 2-1. The synthesis of the active ester of N-Boc protected amino acid was as follows. A linear amino acid with an amino at the terminal and length within 6 carbon atoms (one of glycine, 3-aminopropionic acid, 4-aminobutyric acid, 5-aminopentanoic acid, 6-aminocaproic acid) was saturated in water at room temperature, and di-tert-butyl carbonate dicarbonate (Boc-O-Boc) was added in a molar amount of twice that in in THF to obtain a mixture. The mixture was stirred for a reaction for 2 hours at room temperature followed by an addition of isopropanol to precipitate a large amount of the intermediate product, which was re-dissolved in a minimum amount of DMF. Diethyl ether was added to obtain a precipitate and the dissolution and precipitation were repeated twice to obtain N-Boc protected amino acid. Finally, the N-Boc protected amino acid was dissolved in DMF, followed by an addition of DCC and NHS (a molar ratio 1:1:1), and stirred at room temperature for a reaction overnight. The precipitate was filtered off, and the supernatant was added with diethyl ether to collect a precipitate, which was dissolved in a minimum amount of hot DMF, and precipitated by diethyl ether three times to obtain the active ester of N-Boc protected amino acid.

2-2. The synthesis of N-Boc aminoacyl-Tris was as follows. Trishydroxymethylaminomethane was saturated in water, and was adjusted to pH of 5.8~6.5 with hydrochloric acid. The active ester of N-Boc-protected amino acid dissolved in DMF was added dropwise to the trihydroxymethylaminomethane solution, which was stirred at room temperature overnight. Hydrochloric acid was added to the solution to adjust the pH to 5.0. Then the solution was extracted several times with chloroform and the resulting organic layers were collected and then dried to obtain a residual after the evaporation of chloroform. The residual was dissolved in a large amount of water and extracted with chloroform several times, and the resulting organic layers were collected and dried with the evaporation of the solvent to obtain N—(N'-Boc-aminoacyl)-trishydroxymethylaminomethane.

2-3. N—(N'-Boc-aminoacyl)-trishydroxymethylaminomethane was reacted with the active ester of N,N-dimethylglycine: N—(N'-Boc-aminoacyl)-trishydroxyl aminomethane was saturated in THF and dried. After drying, three times of the molar amount of NaH was added and stirred at room temperature for 2 hours under the conditions isolated from moisture and air. And the saturated THF solution of the active ester of N,N-dimethylglycine was added dropwise for reaction at room temperature overnight. The solution was concentrated under reduced pressure. Diethyl ether was added to collect a precipitate, which was re-dissolved in a minimum amount of THF, and diethyl ether was added again to collect a precipitate. Dissolution in THF and precipitation by diethyl ether was repeated three times to obtain N—(N'-Boc-aminoacyl)-tris-(O—(N, N-two methyglyl))-trihydroxymethyl aminomethane.

Figure 2:
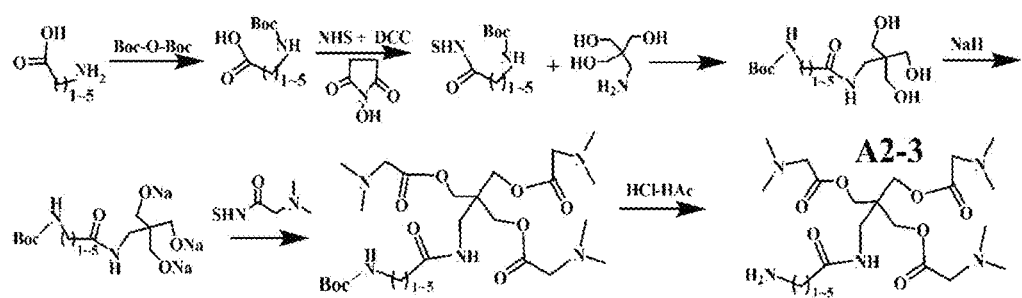
FIG. 2 shows the production of A2-3 type modification agent.

2-4. Preparation of the A2-3 modification agent was as follows. N—(N'-Boc-aminoacyl)-tris-(O—(N,N-dimethylglycyl))-trihydroxymethylaminomethane was dissolved in an acetic acid solution containing 1.0 M HCl, and the mixture was stirred at room temperature for reaction for 3 hours. 10 M cold NaOH solution was added until a large amount of precipitate was observed. The precipitate was dissolved in 10 mM HCl solution and then 10 M cold NaOH solution was added until a large amount of precipitate was observed. The dissolution with acid and precipitation with alkali were repeated three times to obtain the A2-3 modification agent. The reaction route was illustrated in FIG. 2.

Example 3 Preparation of a Representative of A3-1 Modification Agent 3-1. 1,16-bis-Boc-4,7,10,13-tetra-(N,N-dimethylglycyl)-pentaethylenehexaamine was reacted with 1,3-propylsultone as follows. 1,16-bis Boc-4,7,10,13-tetra-(N,N-dimethylgly-cyl)-pentaethylenehexamine obtained in step 1-3 of Example 1 was saturated and dissolved in DMF, and 1,3-propyl sultone was added in a molar amount of four times that of the 1,16-bis Boc-4,7,10,13-tetra-(N,N-dimethylglycyl)-pentaethylenehexamine for reaction at 50° C. for 5 hours. After the reaction, THF was added to collect the precipitate, and the precipitate was washed repeatedly with THF to obtain Boc-protected modification agent A3-1.

3-2. The A3-1 modification agent was prepared as follows. The precipitate obtained in the previous step 3.1 was dissolved in an acetic acid solution containing 1.0 M HCl, and the mixture was stirred at room temperature for reaction for 2 hours. Then the resulting product was concentrated under reduced pressure, and acetone was added to obtain the precipitate. Finally, the process consisting of the dissolution with water and the precipitation with acetone was performed three times to obtain the A3-1 modification agent.

Figure 3:
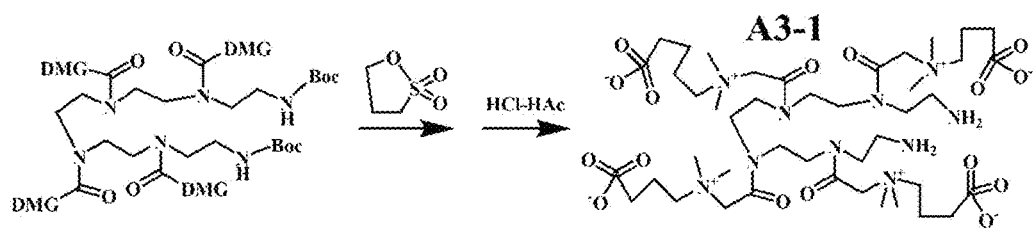
FIG. 3 shows the production of A3-1 type modification agent.

3-3. The reaction route is shown in FIG. 3.

Example 4 Preparation of a Representative of the A4-3 Modification Agent 4-1. N—(N'-Boc-aminoacyl)-tris-(O—(N,N-dimethylglycyl))-trihydroxymethylaminomethane was reacted with 1,3-propyl sultone as follows. N—(N'-Boc-aminoacyl)-O—(N,N-dimethylglycyl)-trishydroxymethylaminomethane obtained in step 2-3 of Embodiment 2 was dissolved in DMF, and 1,3-propyl sultone was added in a molar amount of three times of that of N—(N'-Boc-aminoacyl)-O—(N,N-dimethylglycyl)-trishydroxymethylaminomethane for reaction at 50° C. for 5 hours. Finally, the dissolution with water followed by the precipitation with THF was repeated three times to obtain N-Boc-protected A4-3 modification agent.

4-2. Preparation of the A4-3 modification agent was as follows. The precipitate obtained in the previous step 4.1 was dissolved in an acetic acid containing 1.0 M HCl, and the mixture was stirred at room temperature for a reaction for 2 hours. Then the resulting product was concentrated under increased pressure followed by a precipitation with acetone, and the precipitate was washed with acetone. Finally, the dissolution with water followed by the precipitation with acetone was repeated three times to obtain the target product.

Figure 4:
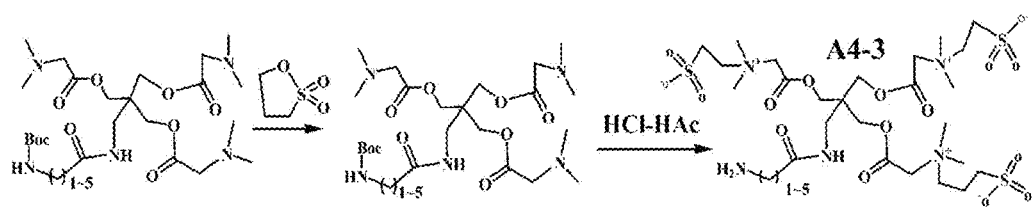
FIG. 4 shows the production of A4-3 type modification agent.

4.3 The reaction route was shown in FIG. 4.

Example 5 Preparation of a Representative A6-2 Modification Agent 5-1. 1,7-N,N-dimethylamino-diethyltriamine was reacted with the active ester of N-Boc protected amino acid as follows. 1,7-N,N-dimethylamino-diethyltriamine was dissolved in DMF, and the THF saturated solution of the active ester of N-Boc protected amino acid prepared in step 2-1 of Embodiment 2 (a molar ratio of 1:1) was added, and the mixture was stirred at room temperature for a reaction for 2 hours. After the reaction, diethyl ether was added to precipitate. Finally, a process consisting of the dissolution with a minimum amount of DMF and the precipitation with diethyl ether was repeated four times to obtain 4-(N'-Boc-aminoacyl)-1,7-N,N-dimethylamino-diethyltriamine.

Figure 5:
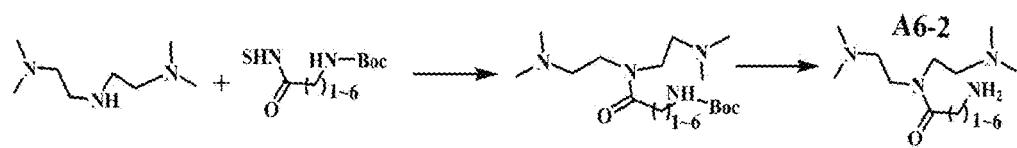
FIG. 5 shows the production of A6-2 type modification agent.

5-2. Preparation of the A6-2 modification agent was as follows. 4-(N'-Boc-aminoacyl)-1,7-N,N-dimethylamino-diethyltriamine was dissolved in an acetic acid containing 1.0 M HCl, and the mixture was stirred at room temperature for a reaction for 2 hours. The resulting product was concentrated under increased pressure followed by a precipitation with THF. Finally, a process consisting of the dissolution with a minimum amount of DMF and the precipitation with THF was repeated three times to obtain the A6-2 modification agent. The reaction route is shown in FIG. 5.

Example 6 Preparation of Representative B1-1, B2-1 and B3-1 Modification Agents 6-1. Esterification with glycine at both terminals of polyethylene glycol 800 (PEG-800) was as follows. The active ester of N-Boc glycine was prepared according to the step 2-1 in Embodiment 2 and then dissolved in THF to produce a saturated N-Boc glycine solution. PEG800 was dissolved in THF, and after the isolation of moisture and air, NaH was added and stirred for 2.0 hours. And then the saturated N-Boc glycine solution was added (excess of 10 times) and then stirred at room temperature overnight. Diethyl ether was added to precipitate; the dissolution with a minimum amount of THF and the precipitation with diethyl ether was repeated three times to obtain PEG800-bis (N-Boc-glycine) ester.

6-2. PEG-800-bis-glycinate: PEG800-bis (N-Boc-glycine) ester was dissolved in an acetic acid solution containing 1.0 M HCl, and the mixture was stirred at room temperature for a reaction for 2 hours, and concentrated the evaporation of water and acetic acid. Diethyl ether was added to precipitate and then a process consisting of the dissolution with a minimum amount of THF and the precipitation with diethyl ether was repeated three times to obtain PEG-800-bis-glycine as the B2-1 modification agent.

6-3. The B1-1 modification agent was prepared as follow. The B2-1 modification agent (PEG-800-bis-glycine ester) was dissolved in THF, and then succinic anhydride in dilute THF solution was added in a molar ratio of 0.5:1 to PEG-800-bis-glycine ester under reflux for a reaction for 6 hours. Diethyl ether was added to precipitate and then a process consisting of the dissolution with a minimum amount of THF and the precipitation with diethyl ether was repeated three times to obtain the B1-1 modification agent.

6-4. The B3-1 modification agent was prepared as follows. PEG-800-monomethyl ether was esterified with the acyl chloride of glycine protected by phthalic anhydride, and then deprotected by hydrazine to obtain the B3-1 modification agent.

Example 7 Preparation of MSP 7-1. Preparation of magnetic fluid was as follows. The magnetic fluid was dispersed with bis-butyl succinate monoester of PEG 800, and the preparation of dispersant and the magnetic fluid was fully referenced to Int J NanoMed, 2013, 8: 791-807.

7-2. Free radical polymerization of W/O microemulsion system was as follows. 0.70 mL of magnetic fluid dispersed with PEG-800-bis-maleic acid monoester was suspended with 2.5 mL of water, and was mixed uniformly with a solution prepared by dissolving 1.5 g of N-hydroxymethyl acrylamide in 4.0 mL of water. Then 1.0 mL of saturated aqueous solution of methyl bisacrylamide was added, and mixed thoroughly with a total volume of about 9 ml. 12 g of AOT was dissolved in 500 mL of n-heptane, and oxygen therein was removed with ultrasonication and nitrogen flow, then was mechanically stirred and mixed as an oil phase. The above aqueous phase of the monomers and magnetic fluids was mixed with the oil phase, and continuously mechanically stirred at a constant speed of 2000 rpm at room temperature for 20 minutes. Then 1.0 mL of ammonium persulfate saturated aqueous solution was added, and stirred for 5 minutes. Finally, 5 µL of N, N'-four ethylenediamine as the catalyst was diluted to 1.0 ml, and then added into the above microemulsion system, and stirred at a constant speed of 2000 rpm and 37° C. for a reaction for 8 hours. The resulting magnetic submicron particle (MSP) precipitated during cooling at room temperature, and then were packed and separated by the magnetic separator. The packed MSP was washed sequentially with a mixture of methanol and acetone (1:9) for three times with 80 mL each time, and with tetrahydrofuran 3 times with 80 mL each, and then with double-distilled water 3 times with 100 mL each followed by suspending in water for use. The total volume and the mass of the product after compaction with the magnetic separator were about 1.0 mL and about 0.10 g, respectively. The amount of MSP was converted accordingly from the compacted volume. The product had a particle size of 0.58 μm, and was abbreviated as MSP.

Figure 6:
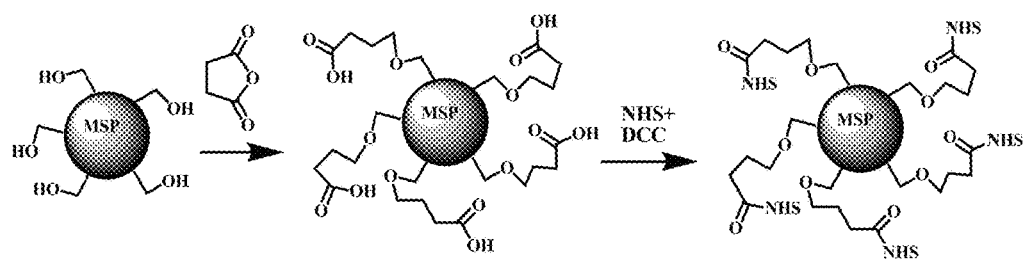
FIG. 6 shows a process of MSP surface carboxylation and carboxyl activation.

Example 8 Carboxylation and Activation of Carboxyl Group on the Surface of MSP 8-1. Carboxylation of pro-carboxyl groups on the surface of MSP was as follows. 0.50 mL of MSP was magnetically compacted in water and suspended in THF, and then the suspension was dried overnight by Na2SO4. 1.2 g of succinic anhydride was added for a refluxing reaction for 8 hours, and then the resulting product was washed repeatedly with THF. Finally, MSP—COOH was obtained. The process was shown in FIG. 6.

8-2. Non-specific adsorptions of water-soluble proteins and small hydrophobic molecules was determined according to Method 2 and Method 3 (Table 1).

8.3. Activation of MSP—COOH to form surface active esters was as follows. The MSP—COOH was dried, and suspended in 10 mL of THF followed by adding of 0.5 g of NHS and 1.0 g of DCC to produce a suspension/mixture. The mixture was shaken overnight at room temperature to obtain MSP active ester (MSP—CO—NHS). The process refers to FIG. 6. The active ester content is about 0.25 mmole/g.

Example 9 Modification Scheme 1 of MSP: Alternate Two-Layer Modification Using Zwitterions and PEG 9-1. Modification with the A1-2 modification agent was as follows. A total of 0.10 mL of MSP—CO—NHS was magnetically compressed in THF, and 0.6 g of the A1-2 modification agent was added to obtain a mixture, and the mixture was shaken at room temperature for a reaction for 6 hours. The resulting product was subjected to magnetic separation and wash by THF, and then was suspended with THF. 0.40 g of the active ester of bromoacetic acid was added, and the suspension was shaken at room temperature for 6 hours followed by washing with THF. Then 0.50 g of 1,3-propyl sultone was added for a reaction at room temperature for 6 hours followed by washing with THF to remove excessive 1,3-propyl sultone. Finally, 1.0 mL of THF solution containing thioglycolic acid was added and the mixture was shaken at room temperature for 6 hours followed by washing with THF to obtain the MSP coated with zwitterions coat and flexible carboxyl (MSP—ZW—COOH).

9-2. Activation of MSP—ZW—COOH was as follows. The MSP—ZW—COOH was suspended in THF followed by adding of 0.15 g of NHS and 0.30 g of DCC and shaking for a reaction at room temperature for 6 hours. The resulting product was washed with THF to obtain the active ester (MSP—ZW—CO—NHS).

Figure 7:
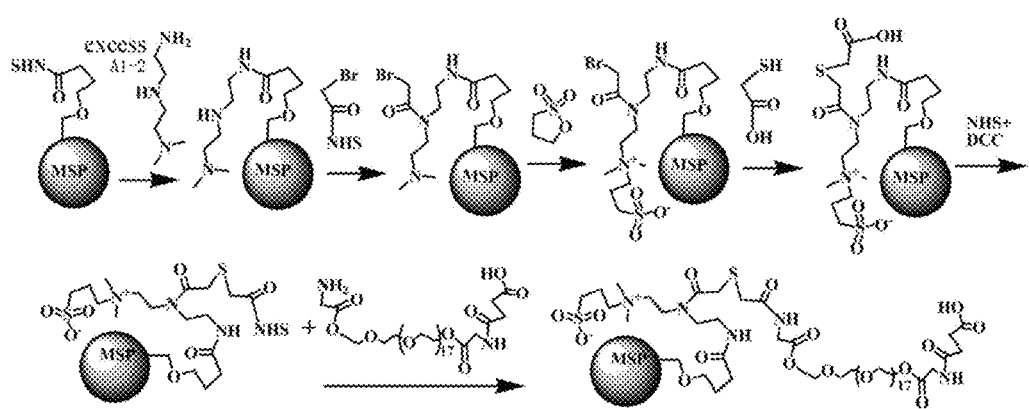
FIG. 7 shows a process of alternate two-layer modification of amphoteric ions and PEG.

9-3. MSP modified with the B1-1 subtype modification agent (PEG800-amino acid) was performed as follows. The MSP—ZW—CO—NHS obtained in step 9-1 was suspended in THF, and a total of 1.5 g of the B1-1 modification agent from PEG800 prepared in step 6-3 of Example 6 was added. The mixture was shaken at room temperature for a reaction for 6 hours, and the resulting product was separated magnetically and washed with THF and water, to obtain the MSP with a two-layer modified carboxyl group (MSP—ZW—PEG-COOH). The process is shown in FIG. 7.

9-4. Non-specific adsorption of water-soluble proteins and small hydrophobic molecules was determined according to Methods 2 and 3 (Table 1).

Example 10 Modification Scheme 2 of MSP: Two-Layer Modification with Zwitterions Alone 10-1. The two-layer modification with 1,7-N,N'-dimethyl-diethyltriamine as an A1-2 modification agent was performed. A total of 0.10 mL of MSP—CO—NHS was collected in THF, and a total of 0.6 g of the A1-2 modification agent was added, and then the suspension was shaken at room temperature for 6 hours. The resulting product was separated magnetically and washed with THF. 0.40 g of the active ester of bromoacetic acid ester was added, and after the suspension was shaken at room temperature for 6 hours. The resulting product was separated magnetically and washed with THF. Then, 0.50 g of 1,3-propyl sultone was added and the suspension was shaken at room temperature for 6 hours followed by magnetic separation and wash with THF. Finally, 1.0 ml of thioglycolic acid was added and the suspension was shaken at room temperature for 6 hours followed by magnetic separation and wash with THF to obtain a zwitterion-modified carboxyl MSP (MSP—ZW—COOH).

10-2. Activation of MSP—ZW—COOH was as follows. The MSP—ZW—COOH was suspended in THF followed by adding of 0.15 g of NHS and 0.3 g of DCC, and the mixture was shaken at room temperature for 6 hours. The resulting product was separated magnetically and washed with THF to obtain the active ester (MSP—ZW—CO—NHS).

Figure 8:
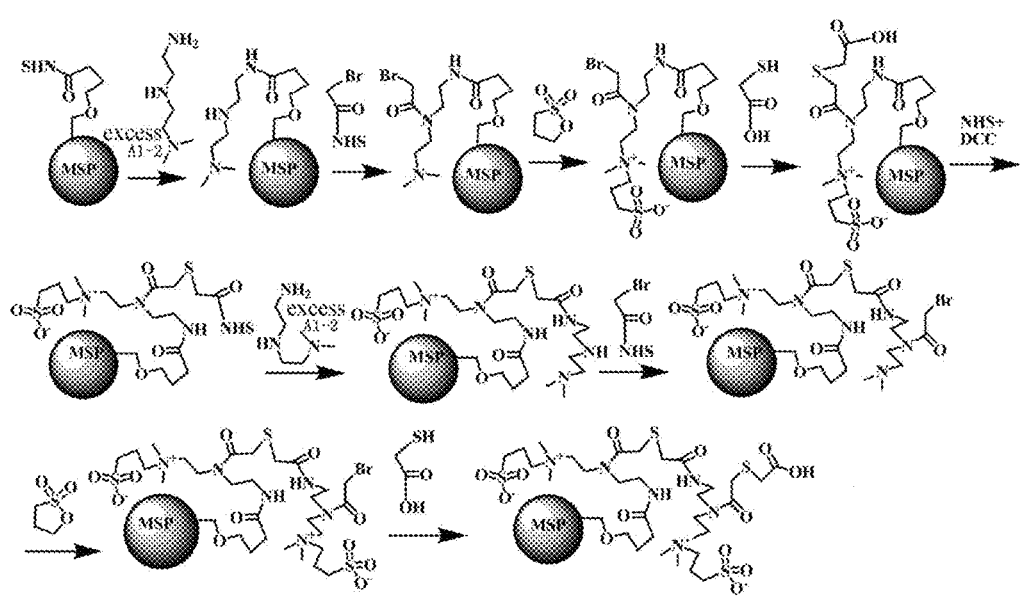
FIG. 8 shows a process using only zwitter ions for two-layer modification.

10-3. Re-modification of the MSP—ZW—CO—NHS was as follows. MSP—ZW—CO—NHS was mixed with 0.6 g of the A1-2 modification agent, and the mixture was processed as the step 10-1 to obtain an MSP product with two-layer modified carboxyl group (MSP—ZW—ZW—COOH). The route is shown in FIG. 8.

10-4. Non-specific adsorption of water-soluble proteins and small hydrophobic molecules was determined according to Methods 2 and 3 (Table 1).

Example 11 Modification Scheme 3 of MSP: Two-Layer Modification with the B1 Type Modification Agent Alone 11-1. Modification with the B1-1 type modification agent (PEG800-amino acid) was as follows. 0.10 mL of MSP—CO—NHS was magnetically packed in THF, and 1.5 g of the B1-1 modification agent in DMF was added. The mixture was shaken at room temperature for 6 hours. The resulting product was magnetically separated and washed with THF to obtain PEG-modified carboxyl group MSP (MSP—PEG-COOH). This modification procedure of the first layer was identical to the step 9-1 of Example 9.

11-2. Activation of the MSP—PEG-COOH was as follows. The MSP—PEG-COOH was suspended in THF, and 0.15 g of NHS and 0.3 g of DCC were added. The mixture was shaken at room temperature for 6 hours, and the resulting product was magnetically separated and washed with THF to obtain the active ester (MSP—PEG-CO—NHS).

11-3. Re-modification with the B1-1 subtype modification agent was as follows. The MSP—PEG-CO—NHS was mixed with 1.5 g of the B1-1 subtype modification agent. After the mixture was processed as mentioned in step 11-1, a two-layer PEG-modified carboxyl group MSP (MSP—PEG-PEG-COOH) was obtained.

11-4. Non-specific adsorption of water-soluble proteins and small hydrophobic molecules was determined according to Methods 2 and 3 (Table 1).

Example 12 Modification Scheme 4 of MSP: Modification with a Modification Agent that is Itself a Zwitterion 12-1. The modification of the first layer was carried out with the A3-1 modification agent. A total of 0.10 mL of MSP—CO—NHS was magnetically packed in THF, and 2.6 g of the modification agent A3-1 were added, and the mixture was shaken at room temperature for 12 hours in suspension. The resulting product was magnetically separated and washed with THF, followed by adding of 1.2 g of succinic anhydride. The mixture was shaken overnight to obtain a carboxyl group MSP (MSP-DZW—COOH) modified directly with zwitterions.

12-3. Activation of carboxyl group and modification of the second layer were as follows. The MSP-DZW—COOH was mixed with 0.15 g of NHS and 0.30 g of DCC in THF, and the suspension was shaken at room temperature for 6 hours. The resulting product was magnetically separated and washed with THF. Then 2.6 g of the A3-1 modification agent was added, and the suspension was shaken for 6 hours followed by magnetic separation and washed with THF. Finally, 1.2 g of succinic anhydride was added for a reaction under shaking overnight to obtain the carboxyl group modified product (MSP-DZW-DZW—COOH).

12-4. Non-specific adsorption of water-soluble proteins and small hydrophobic molecules was determined according to Method 2 and Method 3 (Table 1).

Example 13 Modification Scheme 5 of MSP: Monolayer Co-Modification with Modification Agents to Form Ion Pairs 13-1. Two-layer modification with the A5-1a and A6-1a modification agents was carried out as follows. The A5-1a and A6-1a modification agents were equimolarly mixed, and the modification agent B1-1 was added at a molar ratio of 20% to prepare a ternary mixture modification agent. In THF, a total of 0.10 mL of MSP—CO—NHS was magnetically packed, and mixed with 2.8 g of the ternary mixture modification agent, and the mixture was shaken at room temperature for 6 hours. The resulting product was magnetically separated and washed with THF to obtain a product bearing carboxyl group and ion pair (MSP-(ZW—PEG)-COOH).

13-2. Non-specific adsorption of water-soluble protein (200 mg/g MSP) and small hydrophobic molecules was determined according to Method 2 and Method 3 (Table 1).

Example 14 Characterization of MSP 14-1. Adsorption was carried out with 25 μg of magnetic beads in a MES buffer (pH 6.5) containing 25 ng of ECAP. The adsorbed ECAP was magnetically separated and the activity of bound ECAP was determined, indicating that the modification process of the present disclosure significantly reduces non-specific adsorption (Table 2). The modified MSP had a low non-specific adsorption of ECAP on the surface, which was comparable to the non-specific adsorption capacity of most of the existing commercial MSPs but was better than that of commercialized micron magnetic beads provided by Bangs Laboratories Inc.

14-2. The anti-serum was obtained by immunizing the white rabbit with ECAP. The globulin in the antiserum was precipitated with 30% ammonium sulfate, and then the precipitate was dissolved in 20 mM MES buffer (pH 6.5) followed by dialyzing overnight using the same buffer. The DEAE-Cellulose column was equilibrated with the MES buffer, and the dialyzed globulin was passed through the column to collect the unbound globulin as a polyclonal antibody. 0.50 mg of each of the MSP—COOH was mixed with 0.050 mL of EDC (50 g/L) and 0.050 mL of NHS (50 g/L) dissolved in the MES buffer, and the suspension was shaken at room temperature for 30 min to activate the carboxyl group. After removing the activation agent, 0.15 mg of rabbit polyclonal antibody in the above MES buffer was added, and the suspension was shaken at room temperature for 60 min (at a fixed ratio of less than 10%). Then, the polyclonal antibodies were magnetically separated and combined, and magnetic beads were collected and washed with the above MES buffer. 1.0 μg of each of the fixed polyclonal-antibody functionalized MSP was mixed with 100 ng of ECAP (the binding ratio was less than 6%) dissolved in 20 mM Tris-HCl buffer (pH 7.4), and the resulting mixture was shaken at room temperature for 30 min for absorption. The adsorbed ECAP was magnetically separated and combined, and washed with the aforementioned Tris-HCl buffer twice. 0.20 ml of 4-nitrophenyl phosphate solution prepared by dissolving in 1.0 M Tris-HCl at pH 10.0 was added, and the mixture was shaken at room temperature for 20 min. Finally, 0.050 mL of 5.0 M NaOH solution was added to terminate the ECAP reaction and the magnetic beads were removed. The resulting supernatant was used to determine the absorption at 405 nm, and the amount of the bound ECAP was calculated by assuming the bound ECAP had the same activity with the free ECAP. The binding activity of MSP—ZW—PEG-COOH functionalized with polyclonal antibody to ECAP was significantly higher than that of commercial MSP—COOHs (Table 3). The improvement in the activity of the immobilized polyclonal antibody may be related to the decrease in steric hindrance of the immobilized antibody with the introduction of a flexible linking arm in modification.

14-3. A total of 0.01 g of MSP—ZW—PEG-COOH was activated with DCC and NHS to obtain its active ester in dimethylformamide (DMF). After washing with DMF and suspending in DMF, a DMF solution containing 1.0 mol of ethylenediamine was added and the suspension was firstly shaken rapidly at 4° C. for 30 min and then rapidly shaken again at room temperature for 30 min. After washing with DMF, a MSP with amino functionalized on the surface through a linking arm was obtained. A total of 0.10 g of 2-bromomethacrylic acid (BMAR), was converted to active ester with DCC and NHS in DMF, and then the active esters were mixed with the aforementioned amino-functionalized MSP, the resulting MSP bearing surface BMAR was collected and washed with DMF. Finally, the MSP bearing surface BMAR was washed repeatedly with 20 mM Tris-HCl buffer at pH 7.4 to obtain MSP—ZW—PEG-CO—NH-BMAR whose surface was modified by a protein disulfide selective modification functional group.

14-4. 0.15 mg of the rabbit polyclonal antibody was dissolved in 0.10 mL of 20 mM MES buffer (pH 6.5), and the solution was mixed with 0.010 mL of tricarboxyethylphosphorus solution prepared by dissolving in 20 mM of MES buffer at pH 6.5 to a final concentration of 1.0 mM. The resulting mixture was shaken at room temperature for 30 min, and then mixed with 0.50 mg of MSP—ZW—PEG-CO—NH-BMAR, and the obtained suspension was shaken at room temperature for 60 min. The functionalized MSP was collected for magnetic separation and washed with 20 mM Tris-HCl buffer at pH 7.4. The binding capacity of the functionalized MSP for ECAP was determined by the method referred to 14-2 (Table 3). Clearly, the saturation binding capacity of the antibodies immobilized on MSP—ZW—PEG-CO—NH-BMAR for ECAP was 1.8 times of that of MSP—ZW—PEG-COOH and 4 times of that of Dynal-MSP—COOH.

TABLE 1

Comparison of binding ratios of 4-Nitro-1-naphthol benzoate (NNPB), ECAP and PAAS (n = 2, CV < 12%) to MSPs after covalent modification

| Non-specific absorptive probe | 16 µM NNPB | 64 µM NNPB | ECAP | PAAS |
|---|---|---|---|---|
| MSP | 10% | 16% | 56% | 28% |
| MSP-ZW-PEG-COOH | 4% | 5% | <0.5% | <1% |
| MSP-ZW-ZW-COOH | 1% | 1% | 3% | 3% |
| MSP-PEG-PEG-COOH | 12% | 10% | <1% | <1% |
| MSP-DZW-DZW-COOH | <1% | <1% | <0.5% | 2% |
| MSP-(ZW-PEG)-COOH | 3% | 3% | 1% | 1% |

Table 1 showed that the modification reduced the non-specific adsorption for proteins and small hydrophobic molecules on the surface of micro/nano magnetic materials.

TABLE 2

Comparison of non-specific adsorption of 25 ng ECAP by the modified MSP-COOH and the commercialized MSP-COOH

| Magnetic beads (25 µg) | MSP-ZW-PEG-COOH | MSP-DZW-DZW-COOH | JSR-MSP-COOH | Dynal-MSP-COOH | Bangs-MSP-COOH | Substrate Solution | Full Separation (ECAP) |
|---|---|---|---|---|---|---|---|
| | | | Non-specific absorption | | | | |
| $A_{405}$ (30 min) | 0.292 | 0.295 | 0.355 | 0.293 | 1.732 (diluted 5 times before assay) | 0.293 | 1.786 (5 times dilution) |
| ΔA | — | 0.003 | 0.057 | — | 7.17 (converted) | — | 7.44 (converted) |
| Non-specific absorption of ECAP(25 ng) | Lower than detection period | Lower than detection period | 0.77% | Lower than detection period | 96.3% | Not needed | Not needed |

TABLE 3

Comparison of anti-ECAP polyclonal antibody immobilized on the surface of different magnetic beads for antigen ECAP separation

| Magnetic beads (25 µg) | MSP-ZW-PEG-CO-NH-BMAR | MSP-ZW-PEG-COOH | MSP-DZW-DZW-COOH | JSR-MSP-COOH | Dynal-MSP-COOH | Bangs-MSP-COOH |
|---|---|---|---|---|---|---|
| | The disulfide bond of the polyclonal antibody was reduced by tricarboxyethylphosphine at a final concentration of 1.0 mM in 20 mM MES (pH 6.5), and the reduction reaction mixture was mixed with the MSP under shaken for immobilization for 30 min. | 0.50 mg of each of MSP-COOH was activated with 50 ul of 50 g/L EDC and 50 ul of 50 g/L NHS at room temperature under shaken for 30 min, and then after washing were added with 0.15 mg of the rabbit polyclonal antibodies in 0.10 mL of 20 mM MES buffer at pH 6.5 for reaction for 60 min at room temperature; 1.0 µg of each of the functionalized MSP was tested for the binding of 100 ng of ECAP in Tris-HCl at pH 7.4; the activity of the adsorbed ECAP was measured; and the amount of bound ECAP was calculated (Bangs MSP-COOH was blocked with 5% albumin, and the background adsorption of ECAP after blocking with albumin was corrected) | | | | |
| ECAP bound (mg/g MSP) | 2.0 | 1.1 | 0.7 | 0.1 | 0.4 | 0.3 |

The above embodiments are only used to illustrate the technical solutions and demonstrate the beneficial effects of the present disclosure, and are not intended to be limiting; those of ordinary skill in the art should understand that the technical solutions of the present disclosure may be modified or equivalently substituted without departing from the present disclosure, and such modifications and equivalent substitutions should be covered by the scope of the claims of the present disclosure.

What is claimed is:

1. A method for preparing a product obtained by covalently modifying the surface of a micro/nano material with a hydrophilic material,
comprising:
a) converting a carboxyl group on the surface of the micro/nano material into an active ester, or converting a pro-carboxyl group on the surface of the micro/nano material into a carboxyl group and then into an active ester, or directly converting a pro-carboxyl group on the surface of the micro/nano material into an active ester;
b) forming an amide bond by covalently modifying the micro/nano material on the surface having an active ester obtained in step a by using a modification agent;
c) converting a carboxyl group on the surface of the modified micro/nano material obtained in step b into an active ester, or converting a pro-carboxyl group on the surface of the modified micro/nano material obtained in step b into a carboxyl group and then into an active ester, or directly converting a pro-carboxyl group on the surface of the modified micro/nano material obtained in step b into an active ester; and
d) repeating steps b and c according to the desired numbers of covalently modified layers to obtain a product bearing multilayer covalent modification; wherein upon the last covalent modification, a functional group selected from one or more of a carboxyl group, a pro-carboxyl group, an active ester, a cation, an anion, a neutral hydrophilic group, a metal ion chelating group or a protein-disulfide-selective modification group is formed on the surface of the modified micro/nano material;
wherein in step b, the modification agent is a hydrophilic compound or/and a hydrophilic polymer and comprises an A type modification agent comprising an A1 subtype modification agent and an A2 subtype modification agent and a B type modification agent comprising a B1 subtype modification agent, a B2 subtype modification agent, a B3 subtype modification agent and a B4 subtype modification agent;
the A1 subtype modification agent comprises at least two primary or/and secondary aliphatic amines, and at least one N,N-dialkyl substituted aliphatic tertiary amine selected from N, N-dimethyl substituted aliphatic tertiary amine, N, N-diethyl substituted aliphatic tertiary amine and N, N-di-n-propyl substituted aliphatic tertiary amine; the A2 subtype modification agent comprises one primary or/and secondary aliphatic amine, and at least one N,N-dialkyl substituted aliphatic tertiary amine selected from N, N-dimethyl substituted aliphatic tertiary amine, N, N-diethyl substituted aliphatic tertiary amine and N, N-di-n-propyl substituted aliphatic tertiary amine;
the B type modification agent is free of an N,N-dialkyl substituted aliphatic tertiary amine; the B1 subtype modification agent has a linear structure, with a primary or a secondary aliphatic amine at one end, and a carboxyl group or a pro-carboxyl group at the other end; the B2 subtype modification agent has a linear structure, with primary and/or secondary aliphatic amines at both ends; the B3 subtype modification agent has a linear structure, with a primary aliphatic amine or a secondary aliphatic amine at one end, and a methoxy or ethoxy group at the other end; and the B4 subtype modification agent has a non-linear structure comprising at least two primary and/or secondary aliphatic amines;

for modification, the A type modification agent and the B type modification agent are mixed in any ratio, the sum of the molar amount of the primary and secondary aliphatic amines from the modification agents is in more than 10% excess to that of the active ester on the surface of the modified micro/nano material; unless the last layer of covalent modification is to be realized, a mixture consisting of the A2 subtype modification agent and the B3 subtype modification agent in any ratio is not used in step b; wherein for the A type modification agent, the A1 subtype modification agent is used alone; or a mixture of the A1 subtype modification agent and the A2 subtype modification agent in any ratio is used; and for the B type modification agent, one of the B1, B2 and B4 subtype modification agents, or a mixture thereof in any ratio is used;

wherein in step c, when the A1 or/and A2 subtype modification agent are used in the previous covalent modification, one of the active esters of haloacetic acid, N-bromoacetyl-6-aminocaproate, O-Ts glycolic acid, glycidyl-succinic acid monoester, N-trifluoroacetylglycine, 4-butyraldehyde acid and S-acetyl thioglycolate, or a mixture thereof in any ratio, is used to block the primary aliphatic amine and the secondary aliphatic amine remaining on the surface of the modified material, and then 1,3-propyl sulfonyl ester which is in more than 10% excess to the molar amount of the dialkyl-substituted tertiary amine on the surface of the modified material is used in an inert organic solvent to convert an dialkyl tertiary amine from the A1 and A2 subtype modification agent into a zwitterion in the modification layer, with the quaternary ammonium adjacent to the sulfonic acid; and then the pro-carboxyl group on the surface of the covalently modified product are converted into the active esters; and in step d, in the previous covalent modification, the A2 subtype modification agent is used alone to directly obtain the cationic surface functional group of the alkyl-substituted tertiary amine, an excess of 1,3-propyl sultone is further used to convert the alkyl tertiary amine on the surface of the A2 subtype modification agent into amphoteric ions, with the quaternary ammonium adjacent to the sulfonic acid, to directly obtain a zwitterionic surface functional group; the B3 subtype modification agent is used alone, to directly obtain a neutral and inert hydrophilic surface functional group.

2. The method of claim 1, wherein the micro/nano material to be modified is produced by polymerization reaction of the organic monomers; the organic monomers provide, on the surface of the micro/nano material, a functional group selected from one or more of a carboxyl group, a pro-carboxyl group, an active ester, a cation, an anion, a neutral hydrophilic group, a metal ion chelating group and a protein-disulfide-selective modification group; or the organic monomers provide the carboxyl group or the pro-carboxyl group on the surface of the micro/nano material for derivatization to give those aforementioned functional group.

3. The method of claim 2, wherein the micro/nano material to be modified comprises an organic polymer, an organic polymer-inorganic micro/nanoparticle composite, and an organic polymer-organic micro/nanoparticle composite; micro/nanoparticles in making composite micro/nano material comprise one of magnetic nanoparticles, quantum dots, up-conversion luminescent particles, organic polymer particles and organic-inorganic composite particles, or a mixture thereof;

in the polymerization reaction for making the micro/nano material, specific organic monomers in a covalent structure containing both a functional group for polymerization and a functional group selected from one or more of a carboxyl group, a pro-carboxyl group, an active ester, a cation, an anion, a neutral hydrophilic group, a metal ion chelating group and a protein-disulfide-selective modification group; and a ratio of the specific organic monomers to the total molar amount of monomers is 1% or more;

when making the micro/nano material particles, a water-in-oil or oil-in-water microemulsion system is used to disperse the monomers into microemulsion for polymerization, or large-sized particles/films of polymer materials are mechanically broken to obtain the micro/nano material particles; and when the microemulsion system is used to disperse the monomers followed by polymerization, the specific organic monomers are suitable for single use or mixed use in any ratio as long as their solubility in the polymerization reaction phase satisfies the requirements.

4. The method of claim 1, wherein the functional group selected from one or more of a carboxyl group, a pro-carboxyl group, an active ester, a cation, an anion, a neutral hydrophilic group, a metal ion chelating group or a protein-disulfide-selective modification group is finally formed on the surface of the covalently modified product.

5. The method of claim 1, wherein the A type modification agent further comprises an A3 subtype modification agent, an A4 subtype modification agent, an A5 subtype modification agent and an A6 subtype modification agent; wherein the A3 subtype modification agent has an amphoteric ion pair and at least two primary aliphatic amines and/or secondary aliphatic amines which react with the active ester, or only one primary aliphatic amine or one secondary aliphatic amine which reacts with the active ester and at least one carboxyl group or one pro-carboxyl group;

the A4 subtype modification agent has an amphoteric ion pair, and only one primary aliphatic amine or secondary aliphatic amine which reacts with the active ester, but does not contain the carboxyl group or the pro-carboxyl group suitable for subsequent modification to form the next modification layer; unless the last layer of covalent modification is to be realized, the A4 subtype modification agent is not used alone and is not mixed with the A2 subtype modification agent and the B3 subtype modification agent in any ratio in step b;

the A5 subtype modification agent is an anionic subtype modification agent, the A6 subtype modification agent is a cationic subtype modification agent; the A5 subtype modification agent comprises one or more sulfonic acid anions and/or phosphate anions; the A5 subtype modification agent containing one primary aliphatic amine or secondary aliphatic amine is classified into A5-1; the A5 subtype modification agent containing at least two primary aliphatic amines and/or secondary aliphatic amines is classified into A5-2; the A6 subtype modification agent contains one or more of quaternary ammonium cations or tertiary amine cations; the A6 subtype modification agent containing one primary aliphatic amine or secondary aliphatic amine is classified into A6-1; the A6 subtype modification agent containing at least two primary aliphatic amines and/or secondary aliphatic amines is classified into A6-2; the A5 subtype modification agent and the A6 subtype modification agent are combined for covalent modification of the micro/nano material bearing active ester on the surface to obtain an ion pair-modified layer;

in step b, the A3 subtype modification agent is used alone, or mixed with one or all of the A1 subtype modification agent, the A2 subtype modification agent, the A4 subtype modification agent, the B1 subtype modification agent, the B2 subtype modification agent and the B3 subtype modification agent in any ratio; unless the modification is to be completed, the ratio of the sum of the molar amount of the A1 subtype modification agent, the A3 subtype modification agent, the B1 subtype modification agent and the B2 subtype modification agent in a mixture modification agent is greater than 10%;

in step b, the A4 subtype modification agent is mixed with one or all of the A1 subtype modification agent, the A3 subtype modification agent, the B1 subtype modification agent, the B2 subtype modification agent and the B4 subtype modification agent in any ratio; unless the modification is to be completed, the ratio of the sum of the molar amount of the A1 subtype modification agent, the A3 subtype modification agent, the B1 subtype modification agent, the B2 subtype modification agent and the B4 subtype modification agent in the mixture modification agent is greater than 10%;

in step b, the A5 subtype modification agent and the A6 subtype modification agent are used in combination, and in the mixture of the modification agents, sulfonic acid anions or/and phosphate anions from the A5 subtype modification agent and quaternary ammonium and tertiary amine cations from the A6 subtype modification agent are equivalent in molar amount;

in step b, with any of the modification agents and mixtures thereof in any ratio, if the active ester on the surface of the micro/nano material is derived from CDI or TPG derivatives, the micro/nano material and the modification agents are suspended for reaction in an inert organic solvent or a neutral aqueous solution or in a mixed solvent thereof for modification reaction of 10 minutes or more; or else, the micro/nano material to be modified and the modification agents are suspended for reaction in an inert organic solvent for modification reaction of 10 minutes or more;

in step b, unless the A2 subtype modification agent or the B3 subtype modification agent is used alone or a mixture thereof in any ratio are used, in an inert organic solvent, one of the active esters of haloacetic acid, O-Ts glycolic acid, N-bromoacetyl-6-aminocaproate, N-trifluoroacetylglycine, glycidyl-succinic acid monoester, 4-butyraldehyde acid and S-acetyl thioglycolate, or a mixture thereof in any ratio, is used to react with the primary aliphatic amine and the secondary aliphatic amine on the surface of a modified material to block the amine group on the surface thereof and synchronously obtain the pro-carboxyl group; the molar amount of the active esters are in more than 10% excess to reactive aliphatic amine group on the surface of the modified micro/nano material, to produce halogenated hydrocarbons, O-Ts esters, epoxy groups, trifluoroacetamide groups, aldehyde groups and acetyl protected sulfhydryl groups generated on the surface as the pro-carboxyl groups;

in step c, when the A1 subtype modification agent or the A2 subtype modification agent is not used in the previous covalent modification step, one of the active esters of haloacetic acid, N-bromoacetyl-6-aminocaproic acid, O-Ts hydroxyacetic acid, glycidyl-succinic acid monoester, N-trifluoroacetylglycine, 4-butyraldehyde and S-acetylmercaptoacetic acid, or a mixture thereof in any ratio, is used to block the primary aliphatic amine and the secondary aliphatic amine remaining on the surface of the modified product to obtain a pro-carboxyl group; and the carboxyl group and the pro-carboxyl group on the surface of the covalently modified product are then converted into active esters;

wherein in step c, the active ester on the surface of the covalently modified product reacts with a long linear amino acid to obtain a carboxyl group, or reacts with a linear polyamine containing multiple primary aliphatic amines to obtain an aliphatic amine group for reacting with a material containing a pro-carboxyl group and an active ester to regain pro-carboxyl groups or for reacting with a cyclic anhydride to regain carboxyl group, a linking arm is thus inserted between the surface carboxyl groups or pro-carboxyl groups and the covalently modified product, and then the carboxyl group or pro-carboxyl group derived on the surface of the covalently modified product are further converted to active esters;

in step d, in the previous covalent modification step, when the B1 subtype modification agent having the aliphatic amine group on one end and the carboxyl group on the other end is used alone, carboxyl group is directly obtained on the surface of the modification layer; when one of the B2 subtype modification agent and the B4 subtype modification agent or a mixture thereof in any ratio is used alone, in an inert organic solvent, one of active esters of haloacetic acid ester, O-Ts hydroxyacetic acid ester, N-bromoacetyl-6-aminocaproic acid ester, glycidyl-succinic acid ester, N-trifluoroacetylglycine ester, 4-butyraldehyde acid ester, S-acetylmercaptoacetic acid ester and disulfide-selective modification group corresponding material, or a mixture thereof in any ratio, is used to react with the primary aliphatic amine and the secondary aliphatic amine remaining on the surface of the modified material; and the molar amount of the active esters is in more than 10% excess to the molar amount of the reactive amine groups on the surface of the modified micro/nanomaterial, and one of the corresponding hydrocarbon, O-Ts ester, epoxy, trifluoroacetamide, aldehyde, protecting thiol and disulfide-selective modification group, or a mixture thereof, is generated; and wherein in step d, the carboxyl group or the pro-carboxyl group on the surface of the covalently modified product is converted into an active ester, to react with a long linear amino acid to re-obtain a carboxyl group, or to react with a linear polyamine containing multiple primary aliphatic amines to obtain an aliphatic amine group, for reacting with a material containing a pro-carboxyl group and an active ester to regain a pro-carboxyl group or reacting with a cyclic acid anhydride to regain a carboxyl group or reacting with an active ester containing other functional groups to obtain other forms of surface functional groups, thereby inserting a linking arm between the resulting surface functional groups and the covalently modified product.

6. The method of claim 1, wherein in step d, the protein-disulfide-selective modification group has the following characteristics:

the protein-disulfide-selective modification group comprises two reactive functional groups enabling Michael addition and/or nucleophilic substitution reaction with a sulfhydryl group, with no more than 10 covalent bonds located between the two reactive functional groups, besides a carboxyl group for forming an amide bond with other components;

the reactive group undergoing Michael addition reaction with sulfhydryl group is an acryloyl group, or a vinyl sulfone group, and when functioning alone, acts as a pro-carboxyl group; its reaction center is $\beta$ position of carbonyl in acroleyl group and $\beta$ olefin carbon atom of sulfonyl group;

the reactive group undergoing nucleophilic substitution reaction with a sulfhydryl group is an alkyl containing one or more of chlorine, bromine, iodine, trifluoroacetate, p-toluenesulfonate at $\alpha$-saturated carbon atom of a carbonyl group, a sulfone group, an olefin, and an aromatic ring, and a group from which the alkyl is derived after the Michael-addition of the protein sulfhydryl group, and such a reactive group acting alone is a pro-carboxyl group; chlorine, bromine, iodine, trifluoroacetate, and p-toluenesulfonate are the leaving group X of the nucleophilic substitution reaction, and the reaction center of the nucleophilic substitution is an $\alpha$-saturated carbon atom corresponding to the carbonyl group, the sulfone group, the olefin and the aromatic ring;

wherein in the protein-disulfide-selective modification group, the fragment linking two reaction centers of sulfhydryl groups does not contain a ring or a trialkyl substituent, and a five- or six-membered ring as the covalent linking fragment is attached directly and simultaneously to two functional groups reactive with the protein sulfhydryl groups;

the carboxyl group contained in the protein-disulfide-selective modification group for covalently linking with the micro/nano material, is converted into an active ester, an acid anhydride or an acid chloride to react with the primary and secondary amine on the surface of the micro/nano material, so as to obtain the protein disulfide selective modification functional group on the surface of the modified micro/nano material;

when the protein-disulfide-selective modification group is used, the disulfide bond on the surface of the target protein is first reduced to two spatially adjacent free sulfhydryl groups by trialkylphosphine, and then such two spatially adjacent protein sulfhydryl groups simultaneously react with the two reaction centers in the protein-disulfide-selective modification group on the surface of the modified micro/nano material, thereby achieving site-selective covalent attachment/immobilization for the protein disulfide bond; and wherein the application of the protein-disulfide-selective modification group has the following characteristics: the carboxyl group contained in the protein disulfide selective modification functional group is covalently linked to the amine group of a polymer/small molecule having no sulfhydryl groups and no disulfide bonds on the surface, to obtain the protein-disulfide-selective modification group as a selective modification/labeling agent for disulfide bonds on protein surface; trialkylphosphine is used to reduce the disulfide bond on protein surface to two adjacent free sulfhydryl groups, to simultaneously react with the two reactive groups in the protein-disulfide-selective modification group in the selective modification/labeling agent, thereby achieving the site-specific covalent attachment or labeling.

* * * * *